(12) United States Patent
Yu

(10) Patent No.: US 9,949,952 B2
(45) Date of Patent: *Apr. 24, 2018

(54) METHODS AND COMPOSITIONS FOR TRANSDERMAL DELIVERY

(71) Applicant: Benjamin M. Yu, Plainfield, IL (US)

(72) Inventor: Benjamin M. Yu, Plainfield, IL (US)

(73) Assignee: SPRAYABLE HOLDINGS, INC., Dover, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/724,212

(22) Filed: May 28, 2015

(65) Prior Publication Data
US 2015/0258065 A1 Sep. 17, 2015

Related U.S. Application Data

(63) Continuation of application No. 14/644,039, filed on Mar. 10, 2015.

(60) Provisional application No. 61/950,702, filed on Mar. 10, 2014.

(51) Int. Cl.
| | | |
|---|---|---|
| A61K 31/185 | (2006.01) | |
| A61K 31/195 | (2006.01) | |
| A61K 31/21 | (2006.01) | |
| A61K 31/739 | (2006.01) | |
| A61K 31/4045 | (2006.01) | |
| A61K 47/22 | (2006.01) | |
| A61K 31/385 | (2006.01) | |
| A61K 31/355 | (2006.01) | |
| A61K 31/59 | (2006.01) | |
| A61K 38/06 | (2006.01) | |
| A61K 31/05 | (2006.01) | |
| A61K 31/122 | (2006.01) | |
| A61K 31/015 | (2006.01) | |
| A61K 31/07 | (2006.01) | |
| A61K 31/375 | (2006.01) | |
| A61K 31/714 | (2006.01) | |
| A61K 31/675 | (2006.01) | |
| A61K 31/519 | (2006.01) | |
| A61K 31/145 | (2006.01) | |
| A61K 47/18 | (2017.01) | |
| A61K 9/00 | (2006.01) | |
| A61K 47/10 | (2017.01) | |
| A61K 9/08 | (2006.01) | |
| A61K 9/12 | (2006.01) | |

(52) U.S. Cl.
CPC ........ A61K 31/4045 (2013.01); A61K 9/0014 (2013.01); A61K 9/08 (2013.01); A61K 9/12 (2013.01); A61K 31/015 (2013.01); A61K 31/05 (2013.01); A61K 31/07 (2013.01); A61K 31/122 (2013.01); A61K 31/145 (2013.01); A61K 31/185 (2013.01); A61K 31/355 (2013.01); A61K 31/375 (2013.01); A61K 31/385 (2013.01); A61K 31/519 (2013.01); A61K 31/59 (2013.01); A61K 31/675 (2013.01); A61K 31/714 (2013.01); A61K 38/063 (2013.01); A61K 47/10 (2013.01); A61K 47/18 (2013.01); A61K 47/183 (2013.01); A61K 47/22 (2013.01); A61K 9/0043 (2013.01)

(58) Field of Classification Search
None
See application file for complete search history.

(56) References Cited

U.S. PATENT DOCUMENTS

| | | |
|---|---|---|
| 3,961,060 A | 6/1976 | Fuxe |
| 4,945,094 A | 7/1990 | Salim |
| 6,444,241 B1 | 9/2002 | Tyrpin et al. |
| 7,078,016 B2 | 7/2006 | Rabinowitz |
| 7,560,465 B2 | 7/2009 | Holshen |
| 2003/0027864 A1 | 2/2003 | Guiramand et al. |
| 2003/0165585 A1 | 9/2003 | Mann |
| 2006/0024337 A1 | 2/2006 | Simonnet |
| 2006/0130675 A1 | 6/2006 | Crawford |
| 2009/0253792 A1 | 10/2009 | Mickle et al. |
| 2011/0269689 A1 | 11/2011 | Yu |
| 2013/0267547 A1 | 10/2013 | Gerk et al. |
| 2014/0057873 A1 | 2/2014 | Farber |

FOREIGN PATENT DOCUMENTS

| | | |
|---|---|---|
| CN | 102137839 A | 7/2011 |
| DE | 3800301 A1 | 7/1989 |
| EP | 0552405 A1 | 7/1993 |
| EP | 1952845 A1 | 8/2008 |
| EP | 2499920 A1 | 9/2012 |
| WO | 1993/007870 A1 | 4/1993 |

(Continued)

OTHER PUBLICATIONS

Melatonin PubChem CID 896, pp. 1-11, accessed Nov. 15, 2015 at URL pubchem.ncbi.nlm.nih.gov/compound/Melatonin.*

(Continued)

Primary Examiner — Julie Ha
Assistant Examiner — Kristina M Hellman
(74) Attorney, Agent, or Firm — Perkins Coie LLP; Yingli Wang

(57) ABSTRACT

One aspect of the invention relates to AI-helper compositions comprising an AI compound (e.g., melatonin) and one or more helper esters. The AI-helper compositions disclosed herein can be used for effective transdermal delivery of the AI compound to a subject. Another aspect of the invention relates to applications and preparations of the AI-helper compositions.

17 Claims, 5 Drawing Sheets

(56) References Cited

FOREIGN PATENT DOCUMENTS

| WO | 1995/034280 A1 | 12/1995 |
| WO | 1997/036598 A1 | 10/1997 |
| WO | 2012/069362 A1 | 5/2012 |
| WO | 2014/138708 A1 | 9/2014 |

OTHER PUBLICATIONS

Akers, "Sterile Drug Products: Formulation, Packaging, Manufacturing, and Quality," Informa Healthcare, 16 pp., Chapt. 16 (2010).*

United States Patent and Trademark Office, International Search Report and Written Opinion dated May 29, 2015 for PCT/US2015/019751.

Bansal, S., et al., "Pharmacological Profile of Green Tea and Its Polyphenols: A Review," Med. Chem. Res. 21:3347-3360 (2012).

Bonina, F.P., et al., "Vehicle Effects on In Vitro Skin Permeation of and Stratum Corneum Affinity for Model Drugs Caffeine and Testosterone," Int. J. Pharm. 100:41-47 (1993).

Jing, J., et al., "Equilibrium Partitioning of Drug Molecules Between Aqueous and Amino Acid Ester-Based Ionic Liquids," J. Chem. Thermodynamics 62:27-34 (2013).

Luo, L., et al., "Topical and Transdermal Delivery of Caffeine," Int. J. Pharm. 490:155-164 (2015).

Sinha, V. R., et al., "Permeation Enhancers for Transdermal Drug Delivery," Drug Development and Industrial Pharmacy 26(11):1131-1140 (2000).

United States Patent and Trademark Office, International Preliminary Report on Patentability (Chapter II) dated Feb. 10, 2016 for PCT/US15/19751.

Walters, K. A., et al., "Topical and Transdermal Delivery," Pharmaceutical Preformulation and Formulation: A Practical Guide from Candidate Drug Selection to Commercial Dosage Form, Second Edition, ed. Mark Gibson, Informa Healthcare (2009), Ch. 14, pp. 488-514.

Database WPI, (2017) Clarivate Analytics. Week 199614. Thomson Scientific, London, GB. AN 1996-136188. XP-002773857.

Database WPI, (2017) Clarivate Analytics. Week 201330. Thomson Scientific, London, GB. AN 2013-F73951. XP-002773858.

European Patent Office, Supplementary Partial European Search Reprot dated Sep. 20, 2017 for EP Application No. 15762440.

Janusova, B., et al., "Amino Acid Derivatives as Transdermal Permeation Enhancers," Journal of Controlled Release 165:91-100 (2013).

* cited by examiner

METHODS AND COMPOSITIONS FOR TRANSDERMAL DELIVERY

PRIORITY CLAIM

This application is a continuation of U.S. application Ser. No. 14/644,039, filed Mar. 10, 2015, which claims priority to U.S. Provisional Application No. 61/950,702, filed Mar. 10, 2014, the subject matter of which is hereby incorporated by reference in its entirety, including drawings, as if fully set forth herein.

BACKGROUND

Melatonin is a hormone naturally produced in the human body by the pineal gland. It may play a critical role in preparing the body for sleep. Currently, melatonin is generally taken orally as a sleep aid. However, oral administration of melatonin has various limitations, such as requiring a very high dosage due to the first-pass effect, as well as delivering melatonin unevenly over time.

Alpha-lipoic acid, vitamin E, vitamin D, glutathione, resveratrol, astaxanthin, beta carotene, vitamin A, vitamin C, vitamin B12, vitamin B6, folic acid, and taurine are common and important ingredients in skin care products. However, existing delivery solutions for the ingredients fail to deliver necessary products to all the layers of the skin, and are often only superficial in application.

Consequently, there exists a need for a method for effective, gradual, and safe delivery of melatonin and other compounds mentioned above.

SUMMARY OF THE INVENTION

One aspect of the invention relates to an AI-helper composition comprising a first active ingredient (AI) compound and one or more helper esters. In certain embodiments, for a specific AI, the term "AI" in "AI-helper composition" may be replaced by the specific AI. For example, a melatonin-helper composition means an AI-helper composition as disclosed herein, wherein at least an AI is melatonin.

Another aspect of the invention relates to a method for transdermal administration of the AI-helper composition disclosed herein comprising administering the AI-helper composition disclosed herein to a subject via an administration route selected from the group consisting of transdermal administration, transmucosal administration, trans-nasal administration, topical administration, and any combinations thereof.

Another aspect of the invention relates to a use of the AI-helper composition disclosed herein for the treatments of, e.g., without limitation, skin disorders, gastroesophageal reflux disease, cancer, immune disorders, cardiovascular diseases, depression, seasonal affective disorder (SAD), circadian rhythm sleep disorders, insomnia, Alzheimer's disease, delirium, headaches, obesity, amyotrophic lateral sclerosis, tinnitus, irritable bowel syndrome, aging and autism spectrum disorders (ASD).

DETAILED DESCRIPTION OF THE INVENTION

Figure 1A:
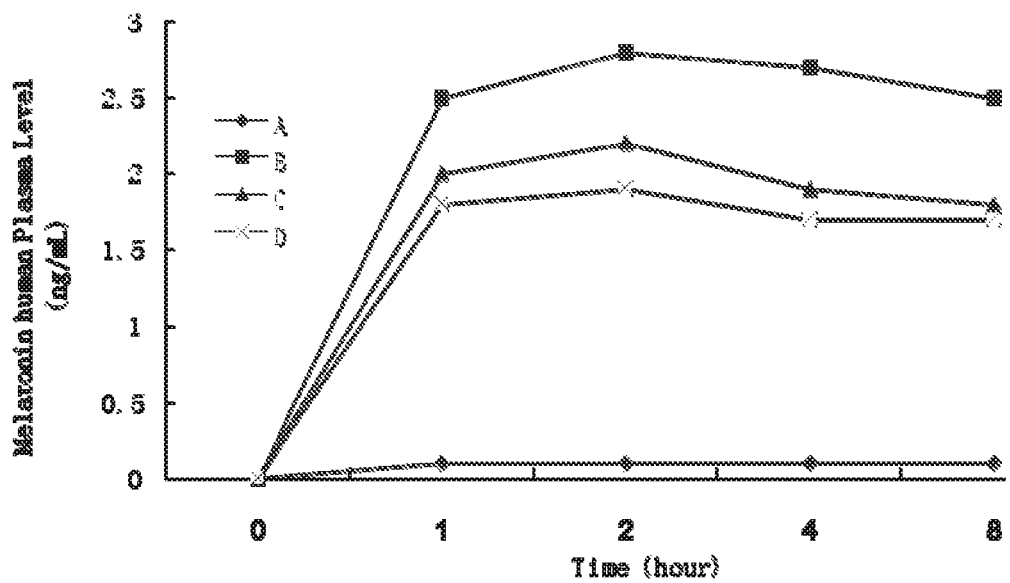
FIG. 1A: Effects of AI-helper compositions comprising tryptophan esters.HCl at various concentrations as disclosed herein on the human skin penetration rate of the AI, wherein the AI is melatonin.

Melatonin has a very low solubility in water (0.1 mg/ml, 0.01%). In certain embodiments, AI-helper compositions disclosed herein can be delivered via an administration route selected from the group consisting of transdermal administration, transmucosal administration, trans-nasal administration, topical administration, and any combinations thereof, which may provide numerous advantages over alternative administration routes (e.g. oral, injection, etc.).

I) AI-HELPER COMPOSITIONS

One aspect of the invention relates to an AI-helper composition comprising a first AI compound and one or more helper esters.

Examples of the AI compounds include, without limitation, melatonin, alpha-lipoic acid, vitamin E, vitamin D, glutathione, resveratrol, astaxanthin, beta carotene, vitamin A, vitamin C, vitamin B12, vitamin B6, folic acid, and taurine.

1) STRUCTURES OF HELPER ESTERS

As used herein, a helper ester can include the helper ester, one or more pharmaceutically acceptable solvates thereof, one or more pharmaceutically acceptable salts thereof, one or more pharmaceutically acceptable stereoisomers thereof, and any mixtures thereof in any ratios.

In certain embodiments, the helper ester comprises a lipophilic portion and a primary, secondary, or tertiary amine group. Optionally, the primary, secondary, or tertiary amine group may form a salt with an acid that is non-toxic to humans and animals (e.g., without limitation, pharmaceutically acceptable acid, such as HF, HCl, HBr, HI, nitric acid, sulfuric acid, bisulfuric acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid, pamoic acid, etc.).

In certain embodiments, the helper ester comprises a structure of Structure I:

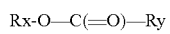   Structure I, including pharmaceutically acceptable solvates thereof, pharmaceutically acceptable salts thereof, and pharmaceutically acceptable stereoisomers thereof, further including mixtures thereof in all ratios, wherein:

Rx is selected from the group consisting of H, alkyl, cycloalkyl, heterocycloalkyl, aryl, heteroaryl, alkoxyl, alkylthio, alkylamino, perfluoroalkyl, alkyl halide, substituted alkyl, substituted cycloalkyl, substituted heterocycloalkyl, substituted aryl, substituted heteroaryl, substituted alkoxyl, substituted alkylthio, substituted alkylamino, substituted perfluoroalkyl, substituted alkyl halide, and

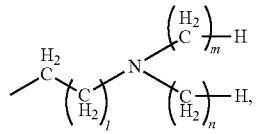

wherein any carbon or hydrogen may be further independently replaced with O, S, P, NRz, or any other pharmaceutically acceptable groups;

Rz is selected from the group consisting of H, alkyl, cycloalkyl, heterocycloalkyl, aryl, heteroaryl, alkoxyl, alkylthio, alkylamino, perfluoroalkyl, alkyl halide, substituted alkyl, substituted cycloalkyl, substituted heterocycloalkyl, substituted aryl, substituted heteroaryl, substituted alkoxyl, substituted alkylthio, substituted alkylamino, substituted perfluoroalkyl, and substituted alkyl halide;

each l, m, and n is independently selected from the group consisting of 0, 1, 2, 3, 4, 5, 6, 7, 8, 9, and 10;

Ry is 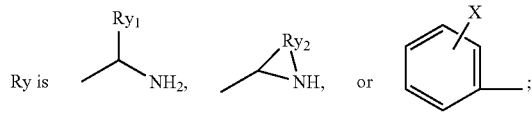

$Ry_1$ is selected from the group consisting of H, alkyl, alkyl further substituted with aryl, heteroaryl, amino, hydroxide, hydroxide aryl, hydroxide carbonyl, amino carbonyl, thiol, alkyl-S— and guanidinyl group;

$Ry_2$ is alkyl;

X is selected from the group consisting of H, $NH_2$, $NHR_5$, OH, $OCOR_5$, Cl, Br, I, CN, $R_5COS$, $R_5O$, $R_5OCONH$, $CH_2NHR_5$, $R_5SO_2$, $R_5SO$, $NH_2SO_2$, and $NO_2$; and each $R_5$ is independently selected from the group consisting of H, alkyl, cycloalkyl, heterocycloalkyl, aryl, heteroaryl, alkoxyl, alkylthio, alkylamino, perfluoroalkyl, alkyl halide, substituted alkyl, substituted cycloalkyl, substituted heterocycloalkyl, substituted aryl, substituted heteroaryl, substituted alkoxyl, substituted alkylthio, substituted alkylamino, substituted perfluoroalkyl, and substituted alkyl halide, wherein any carbon or hydrogen may be further independently replaced with O, S, P, NRz, or any other pharmaceutically acceptable groups.

In certain embodiments, the helper ester comprises a structure of Structure I, including pharmaceutically acceptable solvates thereof, pharmaceutically acceptable salts thereof, and pharmaceutically acceptable stereoisomers thereof, further including mixtures thereof in all ratios, wherein:

Rx is

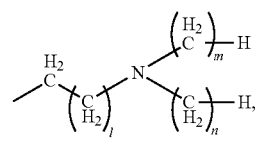

Ry is

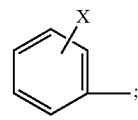

and l, m, n, and X are defined the same as supra.

In certain embodiments, the helper ester comprises a structure of Structure I, including pharmaceutically acceptable solvates thereof, pharmaceutically acceptable salts thereof, and pharmaceutically acceptable stereoisomers thereof, further including mixtures thereof in all ratios,

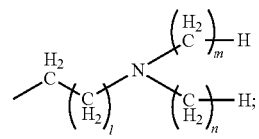

wherein Rx is
Ry is

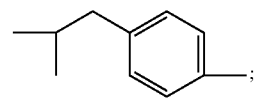

and l, m, and n are defined the same as supra.

In certain embodiments, the helper ester comprises a structure of Structure I, including pharmaceutically acceptable solvates thereof, pharmaceutically acceptable salts thereof, and pharmaceutically acceptable stereoisomers thereof, further including mixtures thereof in all ratios, wherein:

Rx is selected from the group consisting of H, alkyl, cycloalkyl, heterocycloalkyl, aryl, heteroaryl, alkoxyl, alkylthio, alkylamino, perfluoroalkyl, alkyl halide, substituted alkyl, substituted cycloalkyl, substituted heterocycloalkyl, substituted aryl, substituted heteroaryl, substituted alkoxyl, substituted alkylthio, substituted alkylamino, substituted perfluoroalkyl, and substituted alkyl halide, wherein any carbon or hydrogen may be further independently replaced with O, S, P, NRz, or any other pharmaceutically acceptable groups;

Ry is

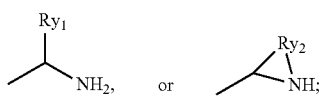

and

Ry$_1$, Ry$_2$ and Rz are defined the same as supra.

In certain embodiments of the invention, the helper esters are selected from the group consisting of Structure 1, Structure 2, Structure 3, Structure 4, Structure 5, Structure 6, Structure 7, Structure 8, Structure 9, Structure 10, Structure 11, Structure 12, Structure 13, Structure 14, Structure 15, Structure 16, and Structure 17:

Structure 1

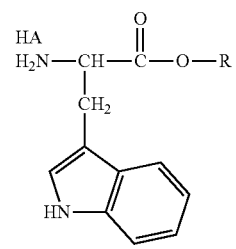

Structure 2

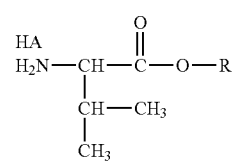

Structure 3

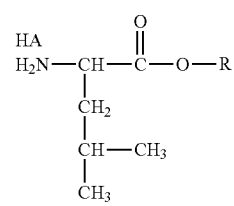

Structure 4

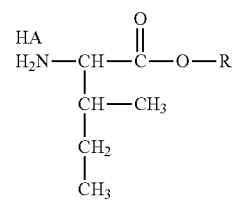

Structure 5

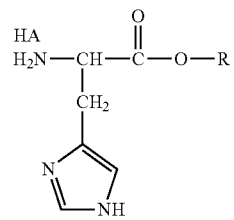

Structure 6

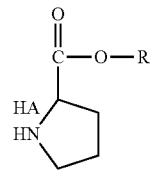

Structure 7

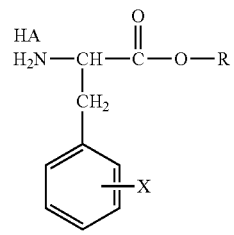

Structure 8

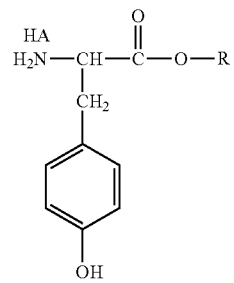

Structure 9

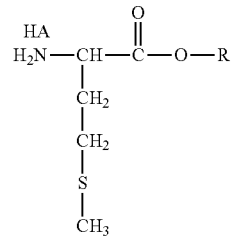

Structure 10

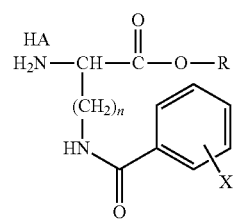

-continued

Structure 11

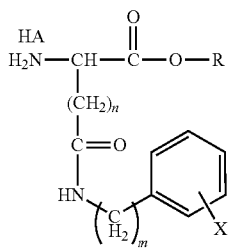

Structure 12

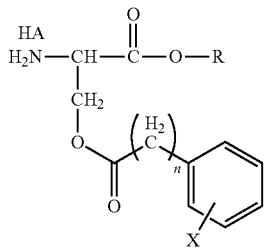

Structure 13

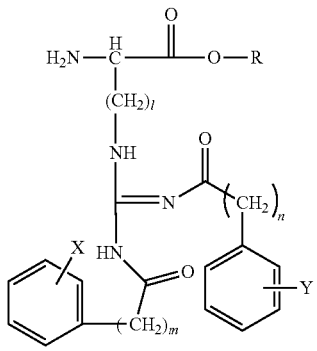

Structure 14

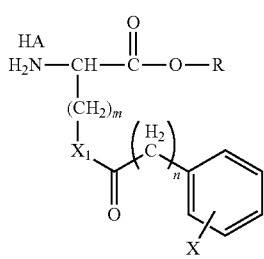

Structure 15

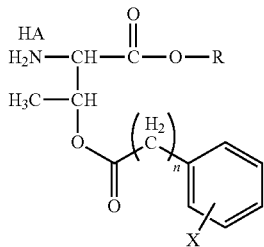

Structure 16

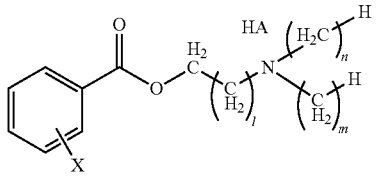

Structure 17

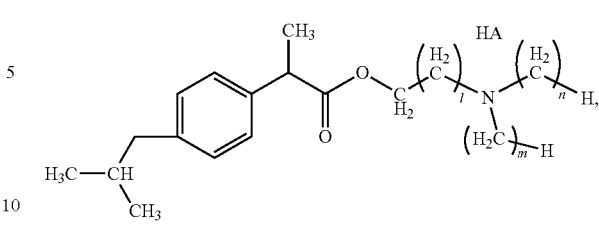

wherein:

each X and Y are independently selected from the group consisting of H, $NH_2$, $NHR_5$, OH, $OCOR_5$, Cl, Br, I, CN, $R_5COS$, $R_5O$, $R_5OCONH$, $CH_2NHR_5$, $R_5SO_2$, $R_5SO$, $NH_2SO_2$, and $NO_2$;

each $X_1$ is independently selected from the group consisting of O, S, $NH_2$, and $NHR_5$;

each $R_1$, $R_5$ and R is independently selected from the group consisting of H, alkyl, cycloalkyl, heterocycloalkyl, aryl, heteroaryl, alkoxyl, alkylthio, alkylamino, perfluoroalkyl, alkyl halide, substituted alkyl, substituted cycloalkyl, substituted heterocycloalkyl, substituted aryl, substituted heteroaryl, substituted alkoxyl, substituted alkylthio, substituted alkylamino, substituted perfluoroalkyl, and substituted alkyl halide, wherein any carbon or hydrogen may be further independently replaced with O, S, P, NRz, or any other pharmaceutically acceptable groups;

each HA is independently a suitable organic acid or a suitable inorganic acid as described below, or independently selected from the group consisting of HF, HCl, HBr, HI, acetic acid, citric acid, benzoic acid, lactic acid, nitric acid, sulfuric acid, bisulfuric acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid, pamoic acid and any other acid that is non-toxic to humans and animals;

each l, m, and n is independently selected from the group consisting of 0, 1, 2, 3, 4, 5, 6, 7, 8, 9, and 10; and each Rz is defined the same as supra.

In certain embodiments, the helper esters selected from the group consisting of Structure 1, Structure 2, Structure 3, Structure 4, Structure 5, Structure 6, Structure 7, Structure 8, Structure 9, Structure 10, Structure 11, Structure 12, Structure 13, Structure 14, Structure 15, Structure 16, and Structure 17 as described supra may further include pharmaceutically acceptable solvates thereof, pharmaceutically acceptable salts thereof, and pharmaceutically acceptable stereoisomers thereof, further including mixtures thereof in all ratios.

Examples of the helper esters disclosed herein include, without limitation, L-tryptophan esters, L-leucine esters, L-isoleucine esters, L-proline esters, L-tyrosine esters, L-phenylalanine esters, L-arginine esters, L-alanine esters, L-asparagine esters, L-aspartic acid esters, L-cysteine esters, L-glutamine esters, L-histidine esters, L-lysine esters, L-methionine esters, L-serine esters, L-threonine esters, L-valine esters, D-tryptophan esters, D-leucine esters, D-isoleucine esters, D-proline esters, D-tyrosine esters, D-phenylalanine esters, D-arginine esters, D-alanine esters, D-asparagine esters, D-aspartic acid esters, D-cysteine esters, D-glutamine esters, D-histidine esters, D-lysine esters, D-methionine esters, D-serine esters, D-threonine esters, D-valine esters, glycine esters, esters of (dialkylamino)alkyl 2-(4-isobutylphenyl)propionate (and salts thereof, e.g. hydrochloride), and esters of (dialkylamino)alkyl 2-acetoxybenzoate hydrochloride (and salts thereof, e.g. hydrochloride), pharmaceutically acceptable solvates thereof, pharmaceutically acceptable salts thereof, and pharmaceutically acceptable stereoisomers thereof, further including mixtures thereof in all ratios.

In certain embodiments, the molar ratio of the one or more helper esters to the AI compound in the AI-helper composition is about 10:1 to about 1:10, or about 10:1.

In certain embodiments, the amount of the AI compound ranges from about 0.01 percent to about 10 percent, from about 0.1 percent to about 5 percent, from about 0.2 percent to about 3 percent, or from about 0.3 percent to about 1 percent of the AI-helper compositions by weight. Generally, out of 100 percent by weight, the amount of salts of esters of amino acids and other acids present in the AI-helper compositions will range from about 1 percent to about 50 percent, from about 2 percent to about 25 percent, from about 3 percent to about 10 percent, or from about 4 percent to about 7 percent of the AI-helper compositions by weight.

In certain embodiments, the amount of the helper esters ranges from about 1 percent to about 50 percent, from about 2 percent to about 25 percent, from about 3 percent to about 10 percent, or from about 4 percent to about 7 percent of the AI-helper composition by weight.

2) SOLVENT

In certain embodiments, the AI-helper compositions disclosed herein further comprise a pharmaceutically acceptable solvent. The pharmaceutically acceptable solvent may be a pure chemical compound or a mixture of multiple chemical compounds. For example, the pharmaceutically acceptable solvent may comprise water, alcohol, glycine, acetone dimethyl sulfoxide, and any mixtures thereof.

In certain embodiments, the solvent is water. Generally, the amount of water ranges from about 1 percent to about 99 percent, from about 50 percent to about 95 percent, from about 75 percent to about 95 percent, or from about 80 percent to about 95 percent of the AI-helper composition by weight.

In certain embodiments, the solvent comprises water and one or more alcohols (e.g. ethanol, propanol, isopropanol, and butanol). The use of alcohols as a solvent may increase the evaporation rate of the AI-helper composition, consequently decrease the amount of time the AI-helper composition is noticeably wet on the skin. Generally, the amount of the alcohols ranges from about 1 percent to about 99 percent, from about 5 percent to about 75 percent, from about 10 percent to about 50 percent, or from about 10 percent to about 25 percent of the AI-helper compositions by weight.

In certain embodiments, the solvent comprises glycerin, and water and/or one or more alcohols as described supra.

In certain embodiments, the solvent comprises dimethyl sulfoxide (DMSO), and water and/or one or more alcohols as described supra. Generally, the amount of DMSO ranges from about 1 percent to about 80 percent, from about 5 percent to about 70 percent, from about 10 percent to about 50 percent, or from about 20 percent to about 30 percent of the AI-helper compositions by weight.

3) OTHER ADDITIVES

In certain embodiments, the AI-helper compositions disclosed herein further comprise one or more additives.

Examples of additives include, without limitation, menthol, one or more amino acids (e.g. L-tryptophan, L-leucine, L-isoleucine, L-proline, L-tyrosine, L-phenylalanine, L-arginine, L-alanine, L-asparagine, L-aspartic acid, L-cysteine, L-glutamine, L-histidine, L-lysine, L-methionine, L-serine, L-threonine, L-valine, D-tryptophan, D-leucine, D-isoleucine, D-proline, D-tyrosine, D-phenylalanine, D-arginine, D-alanine, D-asparagine, D-aspartic acid, D-cysteine, D-glutamine, D-histidine, D-lysine, D-methionine, D-serine, D-threonine, D-valine, and glycine), one or more adjuvants (e.g. preservatives, wetting agents, emulsifying agents, and dispersing agents), and antibacterial and antifungal agents (e.g. paraben, chlorobutanol, and phenol sorbic acid).

In one example, the additive comprises menthol. In certain embodiments, one or more agents selected from the group consisting of alcohols, acetones, DMSO, and salts of the helper esters disclosed herein may be used to increase the solubility of menthol. The use of menthol may have the additional benefit of eliciting a cooling sensation when applied, which may provide feedback to the user as to where of the body the AI-helper composition has been administered to. Generally, the amount of menthol ranges from about 0.01 percent to about 20 percent, from about 0.1 percent to about 10 percent, from about 1 percent to about 5 percent, or from about 1 percent to about 3 percent of the AI-helper compositions by weight.

In another example, the additive comprises scent agent (e.g. peppermint) to provide a desired scent.

The additional amino acids presented in the AI-helper compositions may be beneficial to the skin (if applied to the skin), especially for amino acids that can act as anti-oxidants (e.g. histidine, cysteine, and tyrosine) to protect the skin from oxidative damage. Generally, the amount of amino acids ranges from about 0.001 percent to about 50 percent, from about 0.01 percent to about 20 percent, from about 0.1 percent to about 10 percent, or from about 0.1 percent to about 2 percent of the AI-helper compositions by weight.

4) EXAMPLES OF AI-HELPER COMPOSITIONS

In certain embodiments, the AI-helper composition disclosed herein comprises a first AI compound (e.g., melatonin, alpha-lipoic acid, vitamin E, vitamin D, glutathione, resveratrol, astaxanthin, beta carotene, vitamin A, vitamin C, vitamin B12, vitamin B6, folic acid, taurine, etc.), one or more solvents, and one or more helper esters, such as esters of amino acids (e.g. L-tryptophan esters, L-leucine esters, L-isoleucine esters, L-proline esters, L-tyrosine esters, L-phenylalanine esters, L-arginine esters, L-alanine esters, L-asparagine esters, L-aspartic acid esters, L-cysteine esters, L-glutamine esters, L-histidine esters, L-lysine esters, L-methionine esters, L-serine esters, L-threonine esters, L-valine esters, D-tryptophan esters, D-leucine esters, D-isoleucine esters, D-proline esters, D-tyrosine esters, D-phenylalanine esters, D-arginine esters, D-alanine esters, D-asparagine esters, D-aspartic acid esters, D-cysteine esters, D-glutamine esters, D-histidine esters, D-lysine esters, D-methionine esters, D-serine esters, D-threonine esters, D-valine esters, glycine esters, etc.), and/or esters of other acids (e.g. 2-(dialkylamino)ethyl 2-(4-isobutylphenyl)propionate hydrochloride, 2-(dialkylamino)alkyl 2-acetoxybenzoate hydrochloride, etc.).

In certain embodiments, the AI-helper composition comprises melatonin, a salt of an ester of tryptophan, leucine, isoleucine, tyrosine, phenylalanine, or proline, and water, wherein the ester is selected from the group consisting of isopropyl ester, ethyl ester, methyl ester, propyl, butyl ester, pentyl ester, hexyl ester, and octyl; and the salt is selected from the group consisting of hydrochlorides, hydrofluorides, hydrobromides, hydroiodides, citrates, acetates, benzoates, lactates, butyrates, sulfates, and phosphates.

In certain embodiments, the AI-helper composition comprises an AI compound, a salt of an isopropyl ester of tryptophan, leucine, isoleucine, tyrosine, or phenylalanine, and water, wherein the AI is selected from the group consisting of alpha-lipoic acid, vitamin E, vitamin D, glutathione, resveratrol, astaxanthin, beta carotene, vitamin A, vitamin C, vitamin B12, vitamin B6, folic acid, and taurine; and the salt is selected from the group consisting of hydrochlorides, hydrofluorides, hydrobromides, hydroiodides, citrates, acetates, benzoates, lactates, butyrates, sulfates, and phosphates.

In certain embodiments, the AI-helper composition comprising D-amino acid esters or L-amino acid esters.

5) DEFINITIONS

As used herein, a compound or a composition that is "pharmaceutically acceptable" is suitable for use in contact with the tissue or organ of a biological subject without excessive toxicity, irritation, allergic response, immunogenicity, or other problems or complications, commensurate with a reasonable benefit/risk ratio. If said compound or composition is to be used with other ingredients, said compound or composition is also compatible with said other ingredients.

As used herein, the term "solvate" refers to a complex of variable stoichiometry formed by a solute (e.g., the helper esters disclosed herein) and a solvent. Such solvents for the purpose of the invention may not interfere with the biological activity of the solute. Examples of suitable solvents include, but are not limited to, water, aqueous solution (e.g. buffer), methanol, ethanol and acetic acid. Preferably, the solvent used is a pharmaceutically acceptable solvent. Examples of suitable pharmaceutically acceptable solvents include, without limitation, water, aqueous solution (e.g. buffer), ethanol and acetic acid. Most preferably, the solvent used is water or aqueous solution (e.g. buffer). Examples for suitable solvates are the mono- or dihydrates or alcoholates of the compound according to the invention.

As used herein, pharmaceutically acceptable salts of a compound refers to any pharmaceutically acceptable acid and/or base additive salt of the compound (e.g. the helper esters disclosed herein). Suitable acids include organic and inorganic acids. Suitable bases include organic and inorganic bases. Examples of suitable inorganic acids include, but are not limited to: hydrochloric acid, hydrofluoric acid, hydrobromic acid, hydroiodic acid, nitric acid, sulfuric acid, bisulfuric acid, phosphoric acid, phosphorous acid, phosphonic acid, and boric acid. Examples of suitable organic acids include but are not limited to: isonicotinic acid, acetic acid, bitartaric acid, trifluoroacetic acid, formic acid, oxalic acid, malonic acid, pantothenic acid, succinic acid, tartaric acid, ascorbic acid, maleic acid, gentisinic acid, saccharic acid, fumaric acid, glutamic acid, methanesulfonic acid, ethanesulfonic acid, trifluoromethanesulfonic acid, benzoic acid, glycolic acid, gluconic acid, glucaronic acid, lactic acid, salicylic acid, citric acid, mandelic acid, benzensulfonic acid, p-toluenesulfonic acid, pamoic acid. Examples of suitable inorganic bases include, but are not limited to: ammonia, hydroxyethylamine and hydrazine. Examples of suitable organic bases include, but are not limited to, methylamine, ethylamine, trimethylamine, triethylamine, ethylenediamine, hydroxyethylamine, morpholine, piperazine and guanidine. The invention further provides for the hydrates and polymorphs of all of the helper esters described herein.

The helper esters disclosed herein may contain one or more chiral atoms, or may otherwise be capable of existing as two or more stereoisomers, which are usually enantiomers and/or diastereomers. Accordingly, the helper esters disclosed herein include mixtures of stereoisomers or mixtures of enantiomers, as well as purified stereoisomers, purified enantiomers, stereoisomerically enriched mixtures, or enantiomerically enriched mixtures. The helper esters disclosed herein also include the individual isomers of the helper esters as well as any wholly or partially equilibrated mixtures thereof. The helper esters disclosed herein also cover the individual isomers of the helper esters as mixtures with isomers thereof in which one or more chiral centers are inverted. Also, it is understood that all tautomers and mixtures of tautomers of the helper esters are included within the scope of the helper esters and preferably the structures corresponding thereto.

Racemates obtained can be resolved into the isomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as camphorsulfonic acid. Also advantageous is enantiomer resolution with the aid of a column filled with an optically active resolving agent. The diastereomer resolution can also be carried out by standard purification processes, such as, for example, chromatography or fractional crystallization.

It is also possible to obtain optically active helper esters by the methods described above by using starting materials which are already optically active.

As used herein, unless specified otherwise, the term "alkyl" means a branched or unbranched, saturated or unsaturated, monovalent or multivalent hydrocarbon group, including saturated alkyl groups, alkenyl groups and alkynyl groups. Examples of alkyls include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene, and dodecylene. In certain embodiments, the hydrocarbon group contains 1 to 20 carbons. In certain embodiments, the hydrocarbon group contains 1 to 10 carbons. In certain embodiments, the hydrocarbon group contains 1 to 8 carbons.

As used herein, unless specified otherwise, the term "cycloalkyl" means an alkyl that contains at least one ring and no aromatic rings. In certain embodiments, a cycloalkyl is a saturated cycloalkyl group. In certain embodiments, a cycloalkyl group comprises unsaturated bonds. Examples of cycloalkyls include, but are not limited to, cyclopropyl, cyclobutyl, cyclopentyl, cyclohexyl, cycloheptyl, cyclooctyl, cyclononyl, cyclodecyl, cycloundecyl, and cyclododecyl. In certain embodiments, the hydrocarbon chain contains 1 to 30 carbons. In certain embodiments, the hydrocarbon group contains 1 to 20 carbons. In certain embodiments, the hydrocarbon group contains 1 to 12 carbons. In certain embodiments, the hydrocarbon group contains 1 to 6 carbons.

As used herein, unless specified otherwise, the term "heterocycloalkyl" means a cycloalkyl wherein at least one ring atom is a non-carbon atom. Examples of the non-carbon ring atom include, but are not limited to, S, O and N.

As used herein, unless specified otherwise, the term "alkoxyl" means an alkyl, cycloalkyl, or heterocycloalkyl, which contains one or more oxygen atoms. Examples of alkoxyl include, but are not limited to, —$CH_2$—OH, —$OCH_3$, —O-alkyl, -alkyl-OH, -alkyl-O-alkyl-, wherein the two alkyls can be the same or different.

As used herein, unless specified otherwise, the term "alkyl halide" means an alkyl, cycloalkyl, or heterocycloalkyl, which contains one or more halogen atoms, wherein the halogen atoms can be either the same or different. The term "halogen" means fluorine, chlorine, bromine or iodine. Examples of alkyl halides include, but are not limited to, -alkyl-F, -alkyl-Cl, -alkyl-Br, -alkyl-I, -alkyl(F)—, -alkyl(Cl)—, -alkyl(Br)— and -alkyl(I)—.

As used herein, unless specified otherwise, the term "alkylthio" means an alkyl, cycloalkyl, or heterocycloalkyl, which contains one or more sulfur atoms. Examples of alkylthios include, but are not limited to, —$CH_2$—SH, —$SCH_3$, —S-alkyl, -alkyl-SH, -alkyl-S-alkyl-, wherein the two alkyls can be either the same or different.

As used herein, unless specified otherwise, the term "alkylamino" means an alkyl, cycloalkyl, or heterocycloalkyl, which contains one or more nitrogen atoms. Examples of alkylaminos include, but are not limited to, —$CH_2$—NH, —$NCH_3$, —N(alkyl)-alkyl, —N-alkyl, -alkyl-$NH_2$, -alkyl-N-alkyl and -alkyl-N(alkyl)-alkyl wherein the alkyls can be either the same or different.

As used herein, unless specified otherwise, the term "alkylcarbonyl" means an alkyl, cycloalkyl, or heterocycloalkyl, which contains one or more carbonyl groups. Examples of alkylcarbonyl groups include, but are not limited to, the aldehyde group (—R'—C(O)—H), the ketone group (—R'—C(O)—R"), the carboxylic acid group (R'—COOH), the ester group (—R"—COO—R'), carboxamide, (—R'"—COO—N(R')R"), the enone group (—R"—C(O)—C(R)=C(R")R'"), the acyl halide group (—R'—C(O)—X) and the acid anhydride group (—R"—C(O)—O—C(O)—R'), wherein R', R", R'" and R" are either the same or different alkyls, cycloalkyls, or heterocycloalkyls.

As used herein, unless specified otherwise, the term "perfluoroalkyl" means an alkyl, cycloalkyl, or heterocycloalkyl, which contains one or more fluoro groups, including, without limitation, perfluoromethyl, perfluoroethyl, and perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur ("heteroaryl"). Examples of aryls include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl, quanidino, and benzothiazolyl.

II) PROPERTIES OF THE AI-HELPER COMPOSITION DISCLOSED HEREIN

A person having ordinary skill in the art would be able to test various helper esters, solvents, additives, and concentrations thereof for optimal results.

The AI-helper compositions disclosed herein have shown significantly improved transdermal delivery of the AI compound, compared to aqueous solution/suspension of the AI compound absent the helper esters, pharmaceutically acceptable solvates thereof, pharmaceutically acceptable salts thereof, and pharmaceutically acceptable stereoisomers thereof as disclosed herein. For example, when applying about the same mole of melatonin to a skin of a subject, the subject's melatonin plasma level can be maintained for about 8 hours or more, with a melatonin plasma level about 5 to about 10 times higher than the subject applied with melatonin absent the helper esters.

The AI-helper compositions can also increase the AI compound's solubility and/or the AI compound's skin penetration rate compared to those absent the helper esters, pharmaceutically acceptable solvates thereof, pharmaceutically acceptable salts thereof, and pharmaceutically acceptable stereoisomers thereof as disclosed herein.

Solubility of melatonin in water at 20° C. is about 2 g/100 mL (i.e. about 103 mM, and 2% (w/v)). In certain embodiments, the presence of helper esters can increase melatonin's solubility to about 3 to about 10 g/100 mL, more than about 3 g/100 mL, more than about 10 g/100 mL, more than about 10 g/100 mL, or more than about 10 g/100 mL, depending on the concentration of the helper esters (e.g. about 150 mM to about 500 mM, or higher) and the temperature (e.g. at 25° C., 20° C., at 10° C.). A person having ordinary skill in the art would be able to test various helper esters and concentrations thereof for optimal results.

Skin penetration rates of AI compounds in the presence of helper esters also increase. For example, at 20° C., such increase can be by about 2 fold or more, about 3 fold or more, about 4 fold or more, about 2-4 fold, or about 3-4 fold, depending on the concentration of the helper esters (e.g. about 150 mM to about 500 mM, or higher), and the concentration of the AI compounds (e.g. about 3 mg/100 mL or higher, about 5 mg/100 mL or higher, about 3 mg/100 mL to about 5 mg/100 mL, or about 6 mg/100 mL or higher). A person having ordinary skill in the art would be able to test various helper esters and concentrations thereof for optimal results.

In certain embodiments, the AI-helper composition comprises an AI compound (e.g., melatonin, alpha-lipoic acid, vitamin E, vitamin D, glutathione, resveratrol, astaxanthin, beta carotene, vitamin A, vitamin C, vitamin B12, vitamin B6, folic acid, taurine, etc.) and one or more helper esters, e.g. esters of amino acids (e.g. L-tryptophan esters, L-leucine esters, L-isoleucine esters, L-proline esters, L-tyrosine esters, L-phenylalanine esters, L-arginine esters, L-alanine esters, L-asparagine esters, L-aspartic acid esters, L-cysteine esters, L-glutamine esters, L-histidine esters, L-lysine esters, L-methionine esters, L-serine esters, L-threonine esters, L-valine esters, D-tryptophan esters, D-leucine esters, D-isoleucine esters, D-proline esters, D-tyrosine esters, D-phenylalanine esters, D-arginine esters, D-alanine esters, D-asparagine esters, D-aspartic acid esters, D-cysteine esters, D-glutamine esters, D-histidine esters, D-lysine esters, D-methionine esters, D-serine esters, D-threonine esters, D-valine esters, glycine esters, etc.), and/or esters of other acids (e.g. 2-(dialkylamino)ethyl 2-(4-isobutylphenyl) propionate hydrochloride, 2-(dialkylamino)alkyl 2-acetoxybenzoate hydrochloride, etc.), and one or more solvents, wherein the AI compound's solubility and/or the AI compound's penetration rate (through, e.g. skin) in such composition have increased significantly compared to those in water absent the helper esters, in various temperatures (e.g. at room temperature) (See, e.g. Tables 1-16).

In certain embodiments, the AI-helper composition comprises an AI compound (e.g., melatonin alpha-lipoic acid, vitamin E, vitamin D, glutathione, resveratrol, astaxanthin, beta carotene, vitamin A, vitamin C, vitamin B12, vitamin B6, folic acid, taurine, etc.), tryptophan isopropyl ester, and water. The solubility of the AI compound in such composition has increased significantly from that in pure water.

In certain embodiments, the AI-helper composition comprising D-amino acid esters or L-amino acid esters may provide similar improvements of the solubility and skin penetration rates of the AI compound. In certain embodiments, the AI-helper composition comprising D-amino acid esters or L-amino acid esters may provide different improvements of the solubility and skin penetration rates of the AI compound.

III) PREPARATION OF THE AI-HELPER COMPOSITION DISCLOSED HEREIN

Another aspect of the invention relates to a method for synthesizing the helper esters disclosed herein comprising reacting a suitable acid and a suitable alcohol in the presence of one or more catalyzers, such as HCl, HBr, oxalyl chloride, sulfone dichloride, etc. Examples of specific ester preparations of one or more embodiments are disclosed below.

IV) APPLICATIONS OF THE AI-HELPER COMPOSITION DISCLOSED HEREIN

Another aspect of this invention relates to a method for using the AI-helper compositions disclosed herein for treating one or more conditions, e.g., without limitation, skin disorders, gastroesophageal reflux disease, cancer, immune disorders, cardiovascular diseases, depression, seasonal affective disorder (SAD), circadian rhythm sleep disorders, insomnia, Alzheimer's disease, delirium, headaches, obesity, amyotrophic lateral sclerosis, tinnitus, irritable bowel syndrome, aging and autism spectrum disorders (ASD). In certain embodiments, the AI-helper composition comprises a therapeutically effective amount of the AI compound (e.g., melatonin, alpha-lipoic acid, vitamin E, vitamin D, glutathione, resveratrol, astaxanthin, beta carotene, vitamin A, vitamin C, vitamin B12, vitamin B6, folic acid, taurine, etc.) for the purpose desired.

The term "skin disorders" as used herein means skin conditions that are not desired, e.g., without limitation, wrinkles, aging, aging spot, acne, rosacea, etc.

The terms "treat," "treating," or "treatment" as used herein with regards to a condition refers to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

A "therapeutically effective amount" of an AI compound or an AI-helper composition as used herein is an amount of a composition that produces a desired effect or a desired therapeutic effect in a subject. The precise therapeutically effective amount is an amount of the compound or composition that will yield the most effective results in terms of therapeutic efficacy in a given subject. This amount will vary depending upon a variety of factors, including but not limited to the characteristics of the therapeutic compound (including, e.g., activity, pharmacokinetics, pharmacodynamics, and bioavailability), the physiological condition of the subject (including, e.g., age, sex, disease type and stage, general physical condition, responsiveness to a given dosage, and type of medication), the nature of the pharmaceutically acceptable carrier or carriers in the composition, and the route of administration. One skilled in the clinical and pharmacological arts will be able to determine a therapeutically effective amount through routine experimentation, namely by monitoring a subject's response to administration of a compound or composition and adjusting the dosage accordingly. For additional guidance, see Remington: The Science and Practice of Pharmacy 21st Edition, Univ. of Sciences in Philadelphia (USIP), Lippincott Williams & Wilkins, Philadelphia, Pa., 2005, the entire disclosure of which is incorporated by reference herein.

In certain embodiments, an AI compound or AI-helper composition as provided herein may be administered one or more times a day. In other embodiments, the compound or composition may be delivered less than once a day. For example, the compound or composition may be administered once a week, once a month, or once every several months. Administration of a compound or composition provided herein may be carried out over a specific treatment period determined in advance, or it may be carried out indefinitely or until a specific therapeutic benchmark is reached. In certain embodiments, dosing frequency may change over the course of treatment. For example, a subject may receive less frequent administrations over the course of treatment as certain therapeutic benchmarks are met.

Another aspect of the invention relates to a method for delivering the AI compound (e.g., melatonin, alpha-lipoic acid, vitamin E, vitamin D, glutathione, resveratrol, astaxanthin, beta carotene, vitamin A, vitamin C, vitamin B12, vitamin B6, folic acid, taurine, etc.) to a subject (e.g. human or animals) comprising applying the AI-helper composition disclosed herein to the subject, wherein the AI-helper composition comprising the AI compound.

1) Transdermal Administration of the AI-Helper Composition Disclosed Herein

In one embodiment, the AI-helper composition is applied transdermally (e.g. via applying to the skin).

For example, the AI-helper composition may be applied via a fine mist or stream of liquid dispensed via a spray bottle to various locations on the skin (e.g. face, neck, upper arms, back, wrists, hip, etc.). In another example, the AI-helper composition is administered transdermally via a roll-on bottle. This method of administration allows for application of the AI-helper composition to a more exact region of the skin.

In certain embodiments, the AI-helper composition is administered by employing a cotton swab soaked with the AI-helper composition. A cotton swab may be dabbed in the AI-helper composition, which is held in a reservoir, and then applied directly to the skin, and this procedure may be repeated as many times as necessary until the desired amount of AI compound composition has been dispensed.

In comparison with oral ingestion, transdermal composition application may be effective at a lower dosage of an AI compound, as transdermal composition avoids the first-pass effect that consumes a significant amount of an AI compound taken orally.

2) Administration Methods of the AI-Helper Composition Disclosed Herein

In certain embodiments, the AI-helper composition disclosed herein is applied to the subject via transdermal administration, transmucosal administration, trans-nasal administration, topical administration, and any combinations thereof.

VI). A KIT COMPRISING ONE OR MORE AI-HELPER COMPOSITIONS DISCLOSED HEREIN

Another aspect of the invention relates to a kit comprising one or more AI-helper compositions disclosed herein. In certain embodiments, the kit further comprising articles used to apply the AI-helper compositions to a subject.

V). ADVANTAGES

In certain embodiments, the solubility and/or skin penetration rate of the AI compound in the AI-helper compositions are greatly increased compared to those of the AI compound in aqueous solution absent the helper esters. Thus, an AI compound composition having higher AI compound concentration may be prepared to allows more AI compound to be applied to a target region of skin than an aqueous AI compound composition without the helper esters disclosed herein. Higher skin penetration rates of AI compound in the AI-helper compositions further facilitates the delivery of the AI compound to a user. These improvements to the solubility and skin penetration rate of the AI compound make the AI-helper compositions viable to a wide range of users.

In certain embodiments, the AI-helper compositions may be applied transdermally with the benefits discussed supra.

In certain embodiments, administration (e.g. transdermal administration) of the melatonin compositions disclosed herein to a subject has provided a relatively steady melatonin plasma level for about 8 hours or more, or about 4 hours or more. This prevents the disadvantage of oral or intravenous ingestion of melatonin, where a large amount of the melatonin is absorbed into the body at the same time. Having a steady rate of permeation as opposed to absorbing all the melatonin at once is desirable as it helps deliver the stimulatory effects of melatonin smoothly over several hours, at once prolonging the effect of the melatonin and also mitigating the risk of overdose from absorbing more melatonin than desirable at one time.

In certain embodiments, the administration methods disclosed herein allow the user to control the amount of the AI compound applied by varying the number of administrations. Unlike AI compound containing drinks, which encourage the imbiber to consume a set amount of liquid and the AI compound, the methods disclosed herein encourage the user to regulate each dose so that they only receive the amount of stimulation they desire from the AI compound, and do not overdose.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

VII). EXAMPLES

Example 1. AI-Helper Compositions Showed Higher AI Compound Solubility and Higher Skin Penetration Rates Compared to Those Absent the Helper Esters Solubility was tested by adding small amounts of AI compound to a set volume of an AI-helper composition at a certain temperature until the AI-helper composition was saturated with the AI compound, and measuring the amount of the AI compound added to calculate the solubility of the AI compound in the AI-helper composition at the temperature.

Penetration rate of AI compound in the AI-helper composition through human skin were measured in vitro by modified Franz cells. A Franz cell had two chambers: the top sample chamber and the bottom receiving chamber. The human skin tissue (450-500 μm thick) that separated the top and the receiving chambers was isolated from the anterior or posterior thigh areas.

TABLE 1

Solubility of melatonin (%, w/v) in melatonin-helper compositions comprising a tryptophan ester hydrochloride (D- or L-isomer) and water

| Tryptophan ester | Isomer | Concentration of tryptophan ester hydrochloride (%, w/v) | Temperature (° C.) | Solubility of melatonin (%, w/v) |
|---|---|---|---|---|
| Tryptophan isopropyl ester | L- | 6 | 20 | >1.3% |
| Tryptophan isopropyl ester | D- | 6 | 20 | >1.3% |
| Tryptophan isopropyl ester | L- | 10 | 20 | >1.5% |
| Tryptophan isopropyl ester | D- | 10 | 20 | >1.5% |
| Tryptophan ethyl ester | L- | 10 | 20 | >1.5% |
| Tryptophan ethyl ester | D- | 10 | 20 | >1.5% |
| Tryptophan butyl ester | L- | 10 | 20 | >1.5% |
| Tryptophan butyl ester | D- | 10 | 20 | >1.5% |
| Tryptophan isopropyl ester | L- | 6 | 10 | >1% |
| Tryptophan isopropyl ester | D- | 6 | 10 | >1% |
| Tryptophan isopropyl ester | L- | 10 | 10 | >1% |
| Tryptophan isopropyl ester | D- | 10 | 10 | >1% |
| Tryptophan ethyl ester | L- | 10 | 10 | >1% |
| Tryptophan ethyl ester | D- | 10 | 10 | >1% |
| Tryptophan butyl ester | L- | 10 | 10 | >1% |
| Tryptophan butyl ester | D- | 10 | 10 | >1% |

TABLE 2

Skin penetration rates of Al compounds in Al-helper compositions comprising an Al compound, a tryptophan ester hydrochloride (D- or L-isomer), and water

| Al compound | Tryptophan ester | Isomer | Concentration of tryptophan ester hydrochloride (%, w/v) | Concentration of Al compound (%, w/v) | Temperature (° C.) | Skin penetration rate of Al compound ($\mu g/cm^2/h$) |
|---|---|---|---|---|---|---|
| Melatonin | Tryptophan isopropyl ester | L- | 6 | 1 | 20 | 16.678 ± 1.567 |
| Melatonin | Tryptophan isopropyl ester | D- | 6 | 1 | 20 | 16.451 ± 1.473 |
| Melatonin | Tryptophan ethyl ester | L- | 6 | 1 | 20 | 16.310 ± 1.236 |
| Melatonin | Tryptophan ethyl ester | D- | 6 | 1 | 20 | 16.011 ± 1.511 |
| Melatonin | Tryptophan butyl ester | L- | 6 | 1 | 20 | 15.676 ± 1.574 |
| Melatonin | Tryptophan butyl ester | D- | 6 | 1 | 20 | 15.457 ± 1.435 |
| Melatonin | Tryptophan pentyl ester | L- | 6 | 1 | 20 | 15.012 ± 1.315 |
| Melatonin | Tryptophan pentyl ester | D- | 6 | 1 | 20 | 15.003 ± 1.513 |
| Melatonin | None | N/A | N/A | 1 (suspension) | 20 | 1.153 ± 0.111 |
| Alpha-lipoic acid | None | N/A | N/A | 0.5 | 25 | 0.071 ± 0.063 |
| Alpha-lipoic acid | Tryptophan isopropyl ester | D- | 6 | 0.5 | 25 | 35.456 ± 2.476 |
| Alpha-lipoic acid | Tryptophan isopropyl ester | L- | 6 | 0.5 | 25 | 36.378 ± 2.978 |
| Vitamin E | None | N/A | N/A | 0.5 | 25 | 0.008 ± 0.008 |
| Vitamin E | Tryptophan isopropyl ester | D- | 6 | 0.5 | 25 | 22.783 ± 3.145 |
| Vitamin E | Tryptophan isopropyl ester | L- | 6 | 0.5 | 25 | 23.657 ± 4.120 |
| Vitamin D | None | N/A | N/A | 0.5 | 25 | 0.102 ± 0.113 |
| Vitamin D | Tryptophan isopropyl ester | D- | 6 | 0.5 | 25 | 15.138 ± 2.179 |
| Vitamin D | Tryptophan isopropyl ester | L- | 6 | 0.5 | 25 | 16.345 ± 2.912 |
| Glutathione | None | N/A | N/A | 0.5 | 25 | 0.008 ± 0.013 |
| Glutathione | Tryptophan isopropyl ester | D- | 6 | 0.5 | 25 | 18.126 ± 3.451 |
| Glutathione | Tryptophan isopropyl ester | L- | 6 | 0.5 | 25 | 17.978 ± 3.479 |
| Resveratrol | None | N/A | N/A | 0.5 | 25 | 0.017 ± 0.021 |
| Resveratrol | Tryptophan isopropyl ester | D- | 6 | 0.5 | 25 | 20.728 ± 3.962 |
| Resveratrol | Tryptophan isopropyl ester | L- | 6 | 0.5 | 25 | 20.177 ± 3.195 |
| Astaxanthin | None | N/A | N/A | 0.5 | 25 | 0.012 ± 0.013 |
| Astaxanthin | Tryptophan isopropyl ester | D- | 6 | 0.5 | 25 | 13.131 ± 2.102 |
| Astaxanthin | Tryptophan isopropyl ester | L- | 6 | 0.5 | 25 | 13.341 ± 2.762 |
| Beta Carotene | None | N/A | N/A | 0.5 | 25 | 0.009 ± 0.013 |
| Beta Carotene | Tryptophan isopropyl ester | D- | 6 | 0.5 | 25 | 11.598 ± 2.173 |
| Beta Carotene | Tryptophan isopropyl ester | L- | 6 | 0.5 | 25 | 11.372 ± 2.326 |
| Vitamin A | None | N/A | N/A | 0.5 | 25 | 0.018 ± 0.012 |
| Vitamin A | Tryptophan isopropyl ester | D- | 6 | 0.5 | 25 | 21.715 ± 3.685 |
| Vitamin A | Tryptophan isopropyl ester | L- | 6 | 0.5 | 25 | 20.977 ± 3.741 |
| Vitamin C | None | N/A | N/A | 0.5 | 25 | 0.007 ± 0.013 |
| Vitamin C | Tryptophan isopropyl ester | D- | 6 | 0.5 | 25 | 11.136 ± 2.385 |
| Vitamin C | Tryptophan isopropyl ester | L- | 6 | 0.5 | 25 | 11.345 ± 2.612 |
| Vitamin B12 | None | N/A | N/A | 0.5 | 25 | 0.007 ± 0.011 |
| Vitamin B12 | Tryptophan isopropyl ester | D- | 6 | 0.5 | 25 | 8.718 ± 3.125 |
| Vitamin B12 | Tryptophan isopropyl ester | L- | 6 | 0.5 | 25 | 8.897 ± 3.211 |
| Vitamin B6 | None | N/A | N/A | 0.5 | 25 | 0.059 ± 0.031 |
| Vitamin B6 | Tryptophan isopropyl ester | D- | 6 | 0.5 | 25 | 17.131 ± 2.332 |
| Vitamin B6 | Tryptophan isopropyl ester | L- | 6 | 0.5 | 25 | 17.251 ± 2.415 |
| Folic acid | None | N/A | N/A | 0.5 | 25 | 0.009 ± 0.011 |
| Folic acid | Tryptophan isopropyl ester | D- | 6 | 0.5 | 25 | 6.725 ± 3.327 |
| Folic acid | Tryptophan isopropyl ester | L- | 6 | 0.5 | 25 | 6.915 ± 3.452 |
| Taurine | None | N/A | N/A | 0.5 | 25 | 0.005 ± 0.008 |
| Taurine | Tryptophan isopropyl ester | D- | 6 | 0.5 | 25 | 9.131 ± 2.321 |
| Taurine | Tryptophan isopropyl ester | L- | 6 | 0.5 | 25 | 9.172 ± 2.117 |

TABLE 3

Solubility of melatonin (%, w/v) in melatonin-helper compositions comprising leucine ester hydrochloride and water

| Leucine ester | Concentration of leucine ester hydrochloride (%, w/v) | Temperature (° C.) | Solubility of melatonin (w/v) |
|---|---|---|---|
| Leucine isopropyl ester | 6 | 20 | >0.6% |
| Leucine isopropyl ester | 10 | 20 | >0.8% |
| Leucine methyl ester | 10 | 20 | >0.8% |
| Leucine hexyl ester | 10 | 20 | >0.6% |
| Leucine isopropyl ester | 6 | 10 | >0.5% |
| Leucine isopropyl ester | 10 | 10 | >0.5% |
| Leucine methyl ester | 10 | 10 | >0.5% |
| Leucine hexyl ester | 10 | 10 | >0.4% |

TABLE 4

Skin penetration rates of Al compounds in Al-helper compositions comprising an Al compound, a leucine ester hydrochloride (D- or L-isomer), and water

| Al compound | Leucine ester | Isomer | Concentration of leucine ester hydrochloride (%, w/v) | Concentration of Al compound (%, w/v) | Temperaure (° C.) | Skin penetration rate of Al compound (μg/cm$^2$/h) |
|---|---|---|---|---|---|---|
| Melatonin | Leucine isopropyl ester | L- | 6 | 0.5 | 20 | 9.371 ± 0.137 |
| Melatonin | Leucine ethyl ester | L- | 6 | 0.5 | 20 | 9.101 ± 0.153 |
| Melatonin | Leucine methyl ester | L- | 6 | 0.5 | 20 | 9.058 ± 0.131 |
| Melatonin | Leucine hexyl ester | L- | 6 | 0.5 | 20 | 8.019 ± 0.181 |
| Melatonin | None | N/A | N/A | 0.5 (a suspension) | 20 | 1.147 ± 0.123 |
| Alpha-lipoic acid | None | N/A | N/A | 0.5 | 25 | 0.051 ± 0.023 |
| Alpha-lipoic acid | Leucine isopropyl ester | D- | 6 | 0.5 | 25 | 27.476 ± 2.116 |
| Alpha-lipoic acid | Leucine isopropyl ester | L- | 6 | 0.5 | 25 | 28.377 ± 2.378 |
| Vitamin E | None | N/A | N/A | 0.5 | 25 | 0.012 ± 0.007 |
| Vitamin E | Leucine isopropyl ester | D- | 6 | 0.5 | 25 | 19.723 ± 3.046 |
| Vitamin E | Leucine isopropyl ester | L- | 6 | 0.5 | 25 | 19.611 ± 3.126 |
| Vitamin D | None | N/A | N/A | 0.5 | 25 | 0.082 ± 0.053 |
| Vitamin D | Leucine isopropyl ester | D- | 6 | 0.5 | 25 | 13.139 ± 2.026 |
| Vitamin D | Leucine isopropyl ester | L- | 6 | 0.5 | 25 | 13.155 ± 2.112 |
| Glutathione | None | N/A | N/A | 0.5 | 25 | 0.011 ± 0.008 |
| Glutathione | Leucine isopropyl ester | D- | 6 | 0.5 | 25 | 14.121 ± 2.131 |
| Glutathione | Leucine isopropyl ester | L- | 6 | 0.5 | 25 | 14.128 ± 2.119 |
| Resveratrol | None | N/A | N/A | 0.5 | 25 | 0.013 ± 0.011 |
| Resveratrol | Leucine isopropyl ester | D- | 6 | 0.5 | 25 | 16.028 ± 2.862 |
| Resveratrol | Leucine isopropyl ester | L- | 6 | 0.5 | 25 | 16.126 ± 3.005 |
| Astaxanthin | None | N/A | N/A | 0.5 | 25 | 0.010 ± 0.008 |
| Astaxanthin | Leucine isopropyl ester | D- | 6 | 0.5 | 25 | 11.134 ± 2.183 |
| Astaxanthin | Leucine isopropyl ester | L- | 6 | 0.5 | 25 | 11.251 ± 2.112 |
| Beta Carotene | None | N/A | N/A | 0.5 | 25 | 0.012 ± 0.011 |
| Beta Carotene | Leucine isopropyl ester | D- | 6 | 0.5 | 25 | 9.501 ± 2.763 |
| Beta Carotene | Leucine isopropyl ester | L- | 6 | 0.5 | 25 | 9.252 ± 2.321 |
| Vitamin A | None | N/A | N/A | 0.5 | 25 | 0.015 ± 0.011 |
| Vitamin A | Leucine isopropyl ester | D- | 6 | 0.5 | 25 | 16.315 ± 3.172 |
| Vitamin A | Leucine isopropyl ester | L- | 6 | 0.5 | 25 | 16.357 ± 3.121 |
| Vitamin C | None | N/A | N/A | 0.5 | 25 | 0.008 ± 0.010 |
| Vitamin C | Leucine isopropyl ester | D- | 6 | 0.5 | 25 | 8.256 ± 2.078 |
| Vitamin C | Leucine isopropyl ester | L- | 6 | 0.5 | 25 | 8.378 ± 2.152 |
| Vitamin B12 | None | N/A | N/A | 0.5 | 25 | 0.008 ± 0.009 |
| Vitamin B12 | Leucine isopropyl ester | D- | 6 | 0.5 | 25 | 6.756 ± 2.325 |
| Vitamin B12 | Leucine isopropyl ester | L- | 6 | 0.5 | 25 | 6.813 ± 3.111 |
| Vitamin B6 | None | N/A | N/A | 0.5 | 25 | 0.029 ± 0.035 |
| Vitamin B6 | Leucine isopropyl ester | D- | 6 | 0.5 | 25 | 13.138 ± 2.131 |
| Vitamin B6 | Leucine isopropyl ester | L- | 6 | 0.5 | 25 | 13.252 ± 2.123 |
| Folic acid | None | N/A | N/A | 0.5 | 25 | 0.007 ± 0.012 |
| Folic acid | Leucine isopropyl ester | D- | 6 | 0.5 | 25 | 5.523 ± 3.012 |
| Folic acid | Leucine isopropyl ester | L- | 6 | 0.5 | 25 | 5.786 ± 3.162 |
| Taurine | None | N/A | N/A | 0.5 | 25 | 0.008 ± 0.009 |
| Taurine | Leucine isopropyl ester | D- | 6 | 0.5 | 25 | 7.231 ± 2.386 |
| Taurine | Leucine isopropyl ester | L- | 6 | 0.5 | 25 | 7.175 ± 2.257 |

TABLE 5

Solubility of melatonin (%, w/v) in melatonin-helper compositions comprising an isoleucine ester hydrochloride and water

| Isoleucine ester | Concentration of isoleucine ester hydrochloride (%, w/v) | Temperature (° C.) | Solubility of melatonin (w/v) |
|---|---|---|---|
| Isoleucine isopropyl ester | 6 | 20 | >0.6% |
| Isoleucine isopropyl ester | 10 | 20 | >0.7% |
| Isoleucine methyl ester | 10 | 20 | >0.7% |
| Isoleucine hexyl ester | 10 | 20 | >0.6% |
| Isoleucine isopropyl ester | 6 | 10 | >0.5% |
| Isoleucine isopropyl ester | 10 | 10 | >0.5% |
| Isoleucine methyl ester | 10 | 10 | >0.5% |
| Isoleucine hexyl ester | 10 | 10 | >0.4% |

TABLE 6

Skin penetration rates of Al compounds in Al-helper compositions comprising an Al compound, an isoleucine ester hydrochloride (D- or L-isomer), and water

| Al compound | Isoleucine ester | Isomer | Concentration of isoleucine ester hydrochloride (%, w/v) | Concentration of Al compound (%, w/v) | Temperature (° C.) | Skin penetration rate of Al compound (µg/cm$^2$/h) |
|---|---|---|---|---|---|---|
| Melatonin | Isoleucine isopropyl ester | L- | 6 | 0.5 | 20 | 9.015 ± 0.161 |
| Melatonin | Isoleucine ethyl ester | L- | 6 | 0.5 | 20 | 9.012 ± 0.148 |
| Melatonin | Isoleucine methyl ester | L- | 6 | 0.5 | 20 | 8.712 ± 0.168 |
| Melatonin | Isoleucine pentyl ester | L- | 6 | 0.5 | 20 | 8.219 ± 0.201 |
| Melatonin | None | N/A | N/A | 0.5 (a suspension) | 20 | 1.147 ± 0.123 |
| Alpha-lipoic acid | None | N/A | N/A | 0.5 | 25 | 0.057 ± 0.036 |
| Alpha-lipoic acid | Isoleucine isopropyl ester | D- | 6 | 0.5 | 25 | 28.013 ± 2.078 |
| Alpha-lipoic acid | Isoleucine isopropyl ester | L- | 6 | 0.5 | 25 | 28.897 ± 2.126 |
| Vitamin E | None | N/A | N/A | 0.5 | 25 | 0.016 ± 0.009 |
| Vitamin E | Isoleucine isopropyl ester | D- | 6 | 0.5 | 25 | 19.321 ± 3.012 |
| Vitamin E | Isoleucine isopropyl ester | L- | 6 | 0.5 | 25 | 19.412 ± 3.076 |
| Vitamin D | None | N/A | N/A | 0.5 | 25 | 0.078 ± 0.037 |
| Vitamin D | Isoleucine isopropyl ester | D- | 6 | 0.5 | 25 | 13.315 ± 2.126 |
| Vitamin D | Isoleucine isopropyl ester | L- | 6 | 0.5 | 25 | 13.425 ± 2.132 |
| Glutathione | None | N/A | N/A | 0.5 | 25 | 0.013 ± 0.011 |
| Glutathione | Isoleucine isopropyl ester | D- | 6 | 0.5 | 25 | 14.581 ± 2.183 |
| Glutathione | Isoleucine isopropyl ester | L- | 6 | 0.5 | 25 | 14.698 ± 2.321 |
| Resveratrol | None | N/A | N/A | 0.5 | 25 | 0.016 ± 0.010 |
| Resveratrol | Isoleucine isopropyl ester | D- | 6 | 0.5 | 25 | 16.318 ± 2.762 |
| Resveratrol | Isoleucine isopropyl ester | L- | 6 | 0.5 | 25 | 16.236 ± 2.805 |
| Astaxanthin | None | N/A | N/A | 0.5 | 25 | 0.013 ± 0.009 |
| Astaxanthin | Isoleucine isopropyl ester | D- | 6 | 0.5 | 25 | 11.354 ± 2.452 |
| Astaxanthin | Isoleucine isopropyl ester | L- | 6 | 0.5 | 25 | 11.431 ± 2.312 |
| Beta Carotene | None | N/A | N/A | 0.5 | 25 | 0.015 ± 0.007 |
| Beta Carotene | Isoleucine isopropyl ester | D- | 6 | 0.5 | 25 | 9.471 ± 2.323 |
| Beta Carotene | Isoleucine isopropyl ester | L- | 6 | 0.5 | 25 | 9.412 ± 2.781 |
| Vitamin A | None | N/A | N/A | 0.5 | 25 | 0.015 ± 0.008 |
| Vitamin A | Isoleucine isopropyl ester | D- | 6 | 0.5 | 25 | 16.515 ± 3.212 |
| Vitamin A | Isoleucine isopropyl ester | L- | 6 | 0.5 | 25 | 16.656 ± 3.021 |
| Vitamin C | None | N/A | N/A | 0.5 | 25 | 0.011 ± 0.008 |
| Vitamin C | Isoleucine isopropyl ester | D- | 6 | 0.5 | 25 | 8.526 ± 2.271 |
| Vitamin C | Isoleucine isopropyl ester | L- | 6 | 0.5 | 25 | 8.369 ± 2.102 |
| Vitamin B12 | None | N/A | N/A | 0.5 | 25 | 0.0011 ± 0.006 |
| Vitamin B12 | Isoleucine isopropyl ester | D- | 6 | 0.5 | 25 | 6.816 ± 2.372 |
| Vitamin B12 | Isoleucine isopropyl ester | L- | 6 | 0.5 | 25 | 6.873 ± 3.061 |
| Vitamin B6 | None | N/A | N/A | 0.5 | 25 | 0.022 ± 0.017 |
| Vitamin B6 | Isoleucine isopropyl ester | D- | 6 | 0.5 | 25 | 13.468 ± 2.211 |
| Vitamin B6 | Isoleucine isopropyl ester | L- | 6 | 0.5 | 25 | 13.632 ± 2.125 |
| Folic acid | None | N/A | N/A | 0.5 | 25 | 0.012 ± 0.007 |
| Folic acid | Isoleucine isopropyl ester | D- | 6 | 0.5 | 25 | 5.598 ± 2.812 |
| Folic acid | Isoleucine isopropyl ester | L- | 6 | 0.5 | 25 | 5.793 ± 3.116 |
| Taurine | None | N/A | N/A | 0.5 | 25 | 0.009 ± 0.007 |
| Taurine | Isoleucine isopropyl ester | D- | 6 | 0.5 | 25 | 7.521 ± 2.312 |
| Taurine | Isoleucine isopropyl ester | L- | 6 | 0.5 | 25 | 7.247 ± 2.076 |

TABLE 7

Solubility of melatonin (%, w/v) in melatonin-helper compositions comprising a tyrosine ester hydrochloride and water

| Tyrosine ester | Concentration of tyrosine ester hydrochloride (%, w/v) | Temperature (° C.) | Solubility of melatonin (w/v) |
|---|---|---|---|
| Tyrosine isopropyl ester | 6 | 20 | >1.1% |
| Tyrosine isopropyl ester | 10 | 20 | >1.3% |
| Tyrosine ethyl ester | 10 | 20 | >1.3% |
| Tyrosine propyl ester | 10 | 20 | >1.3% |
| Tyrosine pentyl ester | 10 | 20 | >1.1% |
| Tyrosine hexyl ester | 10 | 20 | >1% |
| Tyrosine isopropyl ester | 6 | 10 | >0.8% |
| Tyrosine isopropyl ester | 10 | 10 | >0.8% |
| Tyrosine ethyl ester | 10 | 10 | >0.7% |
| Tyrosine propyl ester | 10 | 10 | >0.7% |
| Tyrosine pentyl ester | 10 | 10 | >0.7% |
| Tyrosine hexyl ester | 10 | 10 | >0.6% |

TABLE 8

Skin Penetration rates of melatonin in melatonin-helper compositions comprising a tyrosine ester hydrochloride (D- or L-isomer) and water at 20° C.

| Tyrosine ester | Isomer | Concentration of tyrosine ester hydrochloride (%, w/v) | Concentration of melatonin (%, w/v) | Skin penetration rate of melatonin (μg/cm²/h) |
|---|---|---|---|---|
| Tyrosine isopropyl ester | L- | 6 | 1 | 17.613 ± 1.319 |
| Tyrosine isopropyl ester | D- | 6 | 1 | 17.408 ± 1.128 |
| Tyrosine ethyl ester | L- | 6 | 1 | 16.910 ± 1.285 |
| Tyrosine ethyl ester | D- | 6 | 1 | 16.711 ± 1.106 |
| Tyrosine pentyl ester | L- | 6 | 1 | 15.076 ± 1.179 |
| Tyrosine pentyl ester | D- | 6 | 1 | 15.012 ± 1.156 |
| Tyrosine hexyl ester | L- | 6 | 1 | 14.212 ± 1.215 |
| Tyrosine hexyl ester | D- | 6 | 1 | 14.009 ± 1.254 |
| None | N/A | N/A | 1 (suspension) | 1.153 ± 0.111 |

TABLE 9

Solubility of melatonin (%, w/v) in melatonin-helper compositions comprising a phenylalanine ester hydrochloride and water

| Phenylalanine ester | Concentration of phenylalanine ester hydrochloride (%, w/v) | Temperature (° C.) | Solubility of melatonin (w/v) |
|---|---|---|---|
| Phenylalanine isopropyl ester | 6 | 20 | >0.7% |
| Phenylalanine isopropyl ester | 10 | 20 | >0.8% |
| Phenylalanine methyl ester | 10 | 20 | >0.8% |
| Phenylalanine octyl ester | 10 | 20 | >0.5% |
| Phenylalanine isopropyl ester | 6 | 10 | >0.5% |
| Phenylalanine isopropyl ester | 10 | 10 | >0.6% |
| Phenylalanine methyl ester | 10 | 10 | >0.5% |
| Phenylalanine octyl ester | 10 | 10 | >0.4% |

TABLE 10

Skin penetration rates of AI compounds in AI-helper compositions comprising an AI compound, a phenylalanine ester hydrochloride (D- or L-isomer), and water

| AI compound | Phenylalanine ester | Isomer | Concentration of phenylalanine ester hydrochloride (%, w/v) | Concentration of AI compound (%, w/v) | Temperature (° C.) | Skin penetration rate of AI compound (μg/cm²/h) |
|---|---|---|---|---|---|---|
| Melatonin | Phenylalanine isopropyl ester | L- | 6 | 0.5 | 20 | 8.313 ± 0.113 |
| Melatonin | Phenylalanine ethyl ester | L- | 6 | 0.5 | 20 | 8.267 ± 0.151 |
| Melatonin | Phenylalanine methyl ester | L- | 6 | 0.5 | 20 | 8.005 ± 0.118 |
| Melatonin | Phenylalanine pentyl ester | L- | 6 | 0.5 | 20 | 7.881 ± 0.135 |
| Melatonin | None | N/A | N/A | 0.5 (a suspension) | 20 | 1.147 ± 0.123 |
| Alpha-lipoic acid | None | N/A | N/A | 0.5 | 25 | 0.058 ± 0.047 |
| Alpha-lipoic acid | Phenylalanine isopropyl ester | D- | 6 | 0.5 | 25 | 31.796 ± 3.176 |
| Alpha-lipoic acid | Phenylalanine isopropyl ester | L- | 6 | 0.5 | 25 | 32.878 ± 3.568 |
| Vitamin E | None | N/A | N/A | 0.5 | 25 | 0.016 ± 0.011 |
| Vitamin E | Phenylalanine isopropyl ester | D- | 6 | 0.5 | 25 | 21.363 ± 2.015 |
| Vitamin E | Phenylalanine isopropyl ester | L- | 6 | 0.5 | 25 | 21.357 ± 3.120 |
| Vitamin D | None | N/A | N/A | 0.5 | 25 | 0.072 ± 0.033 |
| Vitamin D | Phenylalanine isopropyl ester | D- | 6 | 0.5 | 25 | 15.478 ± 2.126 |
| Vitamin D | Phenylalanine isopropyl ester | L- | 6 | 0.5 | 25 | 15.327 ± 2.032 |
| Glutathione | None | N/A | N/A | 0.5 | 25 | 0.016 ± 0.009 |
| Glutathione | Phenylalanine isopropyl ester | D- | 6 | 0.5 | 25 | 17.526 ± 2.451 |
| Glutathione | Phenylalanine isopropyl ester | L- | 6 | 0.5 | 25 | 17.358 ± 2.259 |
| Resveratrol | None | N/A | N/A | 0.5 | 25 | 0.015 ± 0.011 |
| Resveratrol | Phenylalanine isopropyl ester | D- | 6 | 0.5 | 25 | 18.745 ± 3.112 |
| Resveratrol | Phenylalanine isopropyl ester | L- | 6 | 0.5 | 25 | 18.978 ± 2.135 |
| Astaxanthin | None | N/A | N/A | 0.5 | 25 | 0.019 ± 0.011 |
| Astaxanthin | Phenylalanine isopropyl ester | D- | 6 | 0.5 | 25 | 12.431 ± 2.178 |
| Astaxanthin | Phenylalanine isopropyl ester | L- | 6 | 0.5 | 25 | 12.341 ± 2.042 |
| Beta Carotene | None | N/A | N/A | 0.5 | 25 | 0.019 ± 0.008 |
| Beta Carotene | Phenylalanine isopropyl ester | D- | 6 | 0.5 | 25 | 10.658 ± 2.003 |
| Beta Carotene | Phenylalanine isopropyl ester | L- | 6 | 0.5 | 25 | 10.772 ± 2.174 |
| Vitamin A | None | N/A | N/A | 0.5 | 25 | 0.026 ± 0.015 |
| Vitamin A | Phenylalanine isopropyl ester | D- | 6 | 0.5 | 25 | 20.015 ± 3.025 |
| Vitamin A | Phenylalanine isopropyl ester | L- | 6 | 0.5 | 25 | 20.177 ± 3.241 |
| Vitamin C | None | N/A | N/A | 0.5 | 25 | 0.017 ± 0.015 |
| Vitamin C | Phenylalanine isopropyl ester | D- | 6 | 0.5 | 25 | 10.378 ± 2.155 |
| Vitamin C | Phenylalanine isopropyl ester | L- | 6 | 0.5 | 25 | 10.301 ± 2.022 |

TABLE 10-continued

Skin penetration rates of Al compounds in Al-helper compositions comprising an Al compound, a phenylalanine ester hydrochloride (D- or L-isomer), and water

| Al compound | Phenylalanine ester | Isomer | Concentration of phenylalanine ester hydrochloride (%, w/v) | Concentration of Al compound (%, w/v) | Temperature (° C.) | Skin penetration rate of Al compound (µg/cm$^2$/h) |
|---|---|---|---|---|---|---|
| Vitamin B12 | None | N/A | N/A | 0.5 | 25 | 0.012 ± 0.006 |
| Vitamin B12 | Phenylalanine isopropyl ester | D- | 6 | 0.5 | 25 | 8.156 ± 2.875 |
| Vitamin B12 | Phenylalanine isopropyl ester | L- | 6 | 0.5 | 25 | 8.236 ± 3.057 |
| Vitamin B6 | None | N/A | N/A | 0.5 | 25 | 0.057 ± 0.011 |
| Vitamin B6 | Phenylalanine isopropyl ester | D- | 6 | 0.5 | 25 | 16.531 ± 2.106 |
| Vitamin B6 | Phenylalanine isopropyl ester | L- | 6 | 0.5 | 25 | 16.751 ± 2.012 |
| Folic acid | None | N/A | N/A | 0.5 | 25 | 0.012 ± 0.007 |
| Folic acid | Phenylalanine isopropyl ester | D- | 6 | 0.5 | 25 | 6.771 ± 2.872 |
| Folic acid | Phenylalanine isopropyl ester | L- | 6 | 0.5 | 25 | 6.757 ± 3.012 |
| Taurine | None | N/A | N/A | 0.5 | 25 | 0.011 ± 0.006 |
| Taurine | Phenylalanine isopropyl ester | D- | 6 | 0.5 | 25 | 8.339 ± 2.178 |
| Taurine | Phenylalanine isopropyl ester | L- | 6 | 0.5 | 25 | 8.372 ± 2.237 |

TABLE 11

Solubility of melatonin (%, w/v) in melatonin-helper compositions comprising a proline ester hydrochloride and water

| Proline ester | Concentration of proline ester hydrochloride (%, w/v) | Temperature (° C.) | Solubility of melatonin (w/v) |
|---|---|---|---|
| Proline isopropyl ester | 6 | 20 | >0.6% |
| Proline isopropyl ester | 10 | 20 | >0.8% |
| Proline methyl ester | 10 | 20 | >0.7% |
| Proline hexyl ester | 10 | 20 | >0.6% |
| Proline isopropyl ester | 6 | 10 | >0.4% |
| Proline isopropyl ester | 10 | 10 | >0.4% |
| Proline methyl ester | 10 | 10 | >0.4% |
| Proline hexyl ester | 10 | 10 | >0.4% |

TABLE 12

Skin penetration rates of melatonin in melatonin-helper compositions comprising a proline ester hydrochloride and water at 20° C.

| Proline ester | Concentration of proline ester hydrochloride (%, w/v) | Concentration of melatonin (%, w/v) | Skin penetration rate of melatonin (µg/cm$^2$/h) |
|---|---|---|---|
| Proline isopropyl ester | 6 | 0.5 | 7.329 ± 0.133 |
| Proline ethyl ester | 6 | 0.5 | 7.238 ± 0.101 |
| Proline methyl ester | 6 | 0.5 | 7.272 ± 0.181 |
| Proline pentyl ester | 6 | 0.5 | 6.971 ± 0.171 |
| None | N/A | 0.5 (suspension) | 1.147 ± 0.123 |

TABLE 13

Solubility of melatonin (%, w/v) in melatonin-helper compositions comprising a (dialkylamino)alkyl 2-acetoxybenzoate hydrochloride (non-amino acid ester) and water

| (Dialkylamino)alkyl 2-acetoxybenzoate | Concentration of (dialkylamino)alkyl 2-acetoxybenzoate hydrochloride (%, w/v) | Temperature (° C.) | Solubility of melatonin (w/v) |
|---|---|---|---|
| 3-(Diethylamino)propyl 2-acetoxybenzoate | 6 | 20 | >0.8% |
| 3-(Diethylamino)propyl 2-acetoxybenzoate | 10 | 20 | >1% |
| 6-(Dimethylamino) hexyl 2-acetoxybenzoate | 10 | 20 | >1% |
| 2-(Dibutylamino)ethyl 2-acetoxybenzoate | 10 | 20 | >1% |
| 3-(Diethylamino)propyl 2-acetoxybenzoate | 6 | 10 | >0.6% |
| 3-(Diethylamino)propyl 2-acetoxybenzoate | 10 | 10 | >0.7% |
| 2-(Diethylamino)ethyl 2-acetoxybenzoate | 10 | 10 | >0.7% |
| 2-(Dimethylamino)ethyl 2-acetoxybenzoate | 10 | 10 | >0.7% |
| 2-(Dibutylamino)ethyl 2-acetoxybenzoate | 10 | 10 | >0.7% |

TABLE 14

Skin Penetration rates of melatonin in melatonin-helper compositions comprising a (dialkylamino)alkyl 2-acetoxybenzoate hydrochloride and water at 20° C.

| (Dialkylamino)alkyl 2-acetoxybenzoate | Concentration of (dialkylamino)alkyl 2-acetoxybenzoate hydrochloride (%, w/v) | Concentration of melatonin (%, w/v) | Skin penetration rate of melatonin (µg/cm$^2$/h) |
|---|---|---|---|
| 3-(Diethylamino)propyl 2-acetoxybenzoate | 6 | 1 | 15.321 ± 1.139 |
| 6-(Dimethylamino)hexyl 2-acetoxybenzoate | 6 | 1 | 13.231 ± 1.131 |
| 2-(Dibutylamino)ethyl 2-acetoxybenzoate | 6 | 1 | 14.279 ± 1.187 |

TABLE 14-continued

Skin Penetration rates of melatonin in melatonin-helper compositions comprising a (dialkylamino)alkyl 2-acetoxybenzoate hydrochloride and water at 20° C.

| (Dialkylamino)alkyl 2-acetoxybenzoate | Concentration of (dialkylamino)alkyl 2-acetoxybenzoate hydrochloride (%, w/v) | Concentration of melatonin (%, w/v) | Skin penetration rate of melatonin ($\mu g/cm^2/h$) |
|---|---|---|---|
| 4-(Dibutylamino)butyl 2-acetoxybenzoate | 6 | 1 | 13.945 ± 1.173 |
| None | N/A | 1 (suspension) | 1.153 ± 0.111 |

TABLE 15

Solubility of melatonin (%, w/v) in melatonin-helper compositions comprising a (dialkylamino)alkyl 2-(4-isobutylphenyl)propionate hydrochloride (non-amino acid ester) and water

| (Dialkylamino)alkyl 2-(4-isobutylphenyl)propionate | Concentration of (dialkylamino)alkyl 2-(4-isobutylphenyl)propionate hydrochloride (%, w/v) | Temperature (° C.) | Solubility of melatonin (w/v) |
|---|---|---|---|
| 5-(Diethylamino)pentyl 2-(4-isobutylphenyl)propionate | 6 | 20 | >0.6% |
| 5-(Diethylamino)pentyl 2-(4-isobutylphenyl)propionate | 10 | 20 | >0.8% |
| 2-(Dimethylamino)ethyl 2-(4-isobutylphenyl)propionate | 10 | 20 | >0.8% |
| (Dipentylamino)methyl 2-(4-isobutylphenyl)propionate | 10 | 20 | >0.7% |
| 2-(Diethylamino)ethyl 2-(4-isobutylphenyl)propionate | 6 | 10 | >0.5% |
| 4-(Diethylamino)butyl 2-(4-isobutylphenyl)propionate | 10 | 10 | >0.5% |
| 3-(Dimethylamino)propyl 2-(4-isobutylphenyl)propionate | 10 | 10 | >0.5% |
| 2-(Dipentylamino)ethyl 2-(4-isobutylphenyl)propionate | 10 | 10 | >0.4% |

TABLE 16

Skin penetration rates of Al compounds in Al-helper compositions comprising an Al compound, a dialkylaminoalkyl 2-(4-isobutylphenyl)propionate hydrochloride, and water

| Al compound | Dialkylaminoalkyl 2-(4-isobutylphenyl)propionate | Concentration of dialkylaminoalkyl 2-(4-isobutylphenyl)propionate hydrochloride (%, w/v) | Concentration of Al compound (%, w/v) | Temperature (° C.) | Skin penetration rate of Al compound ($\mu g/cm^2/h$) |
|---|---|---|---|---|---|
| Melatonin | 5-(Diethylamino)pentyl 2-(4-isobutylphenyl)propionate | 6 | 0.5 | 20 | 10.321 ± 1.145 |
| Melatonin | 2-(Dimethylamino)ethyl 2-(4-isobutylphenyl)propionate | 6 | 0.5 | 20 | 10.239 ± 1.173 |
| Melatonin | (Dipentylamino)methyl 2-(4-isobutylphenyl)propionate | 6 | 0.5 | 20 | 9.271 ± 1.134 |
| Melatonin | 4-(Diethylamino)butyl 2-(4-isobutylphenyl)propionate | 6 | 0.5 | 20 | 9.949 ± 1.158 |
| Melatonin | None | N/A | 0.5 (a suspension) | 20 | 1.147 ± 0.123 |
| Alpha-lipoic acid | None | N/A | 0.5 | 25 | 0.056 ± 0.032 |

TABLE 16-continued

Skin penetration rates of Al compounds in Al-helper compositions comprising an Al compound, a dialkylaminoalkyl 2-(4-isobutylphenyl)propionate hydrochloride, and water

| Al compound | Dialkylaminoalkyl 2-(4-isobutylphenyl)propionate | Concentration of dialkylaminoalkyl 2-(4-isobutylphenyl)propionate hydrochloride (%, w/v) | Concentration of Al compound (%, w/v) | Temperature (° C.) | Skin penetration rate of Al compound (μg/cm$^2$/h) |
|---|---|---|---|---|---|
| Alpha-lipoic acid | 2-(Diethylamino)ethyl 2-(4-isobutylphenyl)propionate | 6 | 0.5 | 25 | 30.478 ± 2.982 |
| Vitamin E | None | N/A | 0.5 | 25 | 0.012 ± 0.006 |
| Vitamin E | 2-(Diethylamino)ethyl 2-(4-isobutylphenyl)propionate | 6 | 0.5 | 25 | 19.783 ± 4.025 |
| Vitamin D | None | N/A | 0.5 | 25 | 0.72 ± 0.063 |
| Vitamin D | 2-(Diethylamino)ethyl 2-(4-isobutylphenyl)propionate | 6 | 0.5 | 25 | 13.179 ± 2.215 |
| Glutathione | None | N/A | 0.5 | 25 | 0.012 ± 0.010 |
| Glutathione | 2-(Diethylamino)ethyl 2-(4-isobutylphenyl)propionate | 6 | 0.5 | 25 | 16.356 ± 3.011 |
| Resveratrol | None | N/A | 0.5 | 25 | 0.015 ± 0.011 |
| Resveratrol | 2-(Diethylamino)ethyl 2-(4-isobutylphenyl)propionate | 6 | 0.5 | 25 | 18.568 ± 3.112 |
| Astaxanthin | None | N/A | 0.5 | 25 | 0.019 ± 0.010 |
| Astaxanthin | 2-(Diethylamino)ethyl 2-(4-isobutylphenyl)propionate | 6 | 0.5 | 25 | 12.331 ± 2.182 |
| Beta Carotene | None | N/A | 0.5 | 25 | 0.015 ± 0.011 |
| Beta Carotene | 2-(Diethylamino)ethyl 2-(4-isobutylphenyl)propionate | 6 | 0.5 | 25 | 10.138 ± 2.381 |
| Vitamin A | None | N/A | 0.5 | 25 | 0.021 ± 0.011 |
| Vitamin A | 2-(Diethylamino)ethyl 2-(4-isobutylphenyl)propionate | 6 | 0.5 | 25 | 18.347 ± 3.132 |
| Vitamin C | None | N/A | 0.5 | 25 | 0.016 ± 0.012 |
| Vitamin C | 2-(Diethylamino)ethyl 2-(4-isobutylphenyl)propionate | 6 | 0.5 | 25 | 10.112 ± 2.322 |
| Vitamin B12 | None | N/A | 0.5 | 25 | 0.016 ± 0.008 |
| Vitamin B12 | 2-(Diethylamino)ethyl 2-(4-isobutylphenyl)propionate | 6 | 0.5 | 25 | 8.127 ± 3.211 |
| Vitamin B6 | None | N/A | 0.5 | 25 | 0.023 ± 0.027 |
| Vitamin B6 | 2-(Diethylamino)ethyl 2-(4-isobutylphenyl)propionate | 6 | 0.5 | 25 | 15.251 ± 2.015 |
| Folic acid | None | N/A | 0.5 | 25 | 0.012 ± 0.007 |
| Folic acid | 2-(Diethylamino)ethyl 2-(4-isobutylphenyl)propionate | 6 | 0.5 | 25 | 6.235 ± 1.356 |
| Taurine | None | N/A | 0.5 | 25 | 0.012 ± 0.006 |
| Taurine | 2-(Diethylamino)ethyl 2-(4-isobutylphenyl)propionate | 6 | 0.5 | 25 | 8.711 ± 1.871 |

Although data shown in Tables 1-16 related to hydrochloride salts of certain helper esters as examples, salts of other acids of helper esters achieved similar effects without significantly altering the AI compounds' solubility or skin penetration rates in the helper ester composition (Tables 17 and 18).

TABLE 17

Solubility of melatonin in a melatonin-helper composition comprising water and a salt of helper esters with different acids (HA) at 20° C.

Different HA salts of tryptophan isopropyl ester

| HA | Concentration of tryptophan isopropyl ester•HA (%, w/v) | Solubility of melatonin (w/v) |
| --- | --- | --- |
| HCl | 10 | >1.5% |
| HF | 10 | >1.5% |
| HBr | 10 | >1.4% |
| HI | 10 | >1.3% |
| Citric acid | 10 | >1.2% |
| acetic acid | 10 | >1.4% |
| benzoic acid | 10 | >1.3% |
| lactic acid | 10 | >1.4% |
| butyric acid | 10 | >1.3% |
| ½$H_2SO_4$ | 10 | >1.4% |
| $H_2SO_4$ | 10 | >1.4% |
| ⅓$H_3PO_4$ | 10 | >1.2% |
| ⅔$H_3PO_4$ | 10 | >1.3% |

Different HA salts of tyrosine isopropyl ester

| HA | Concentration of tyrosine isopropyl ester•HA (%, w/v) | Solubility of melatonin (w/v) |
| --- | --- | --- |
| HCl | 10 | >1.3% |
| HF | 10 | >1.3% |
| HBr | 10 | >1.2% |
| HI | 10 | >1% |
| citric acid | 10 | >1% |
| acetic acid | 10 | >1.1% |
| benzoic acid | 10 | >1% |
| lactic acid | 10 | >1.1% |
| butyric acid | 10 | >1% |
| ½$H_2SO_4$ | 10 | >1% |
| $H_2SO_4$ | 10 | >1.2% |
| ⅓$H_3PO_4$ | 10 | >1.0% |
| ⅔$H_3PO_4$ | 10 | >1.1% |

TABLE 18

Skin penetration rate of melatonin (1%, w/v) or alpha-lipoic acid (0.5%, w/v) in an AI-helper composition comprising various salts of helper esters (6%, w/v) and water at 20° C.

Tryptophan isopropyl ester•HA

| HA | Skin penetration rate of melatonin ($\mu g/cm^2/h$) |
| --- | --- |
| HCl | 16.678 ± 1.567 |
| HF | 16.165 ± 1.167 |
| HBr | 15.971 ± 1.785 |
| HI | 14.467 ± 1.183 |
| Citric acid | 15.371 ± 1.287 |
| Acetic acid | 15.456 ± 1.712 |
| Benzoic acid | 14.665 ± 1.589 |
| Lactic acid | 15.897 ± 1.109 |
| Butyric acid | 15.378 ± 1.598 |
| ½$H_2SO_4$ | 15.928 ± 1.476 |
| $H_2SO_4$ | 16.780 ± 1.891 |
| ⅓$H_3PO_4$ | 15.321 ± 1.497 |
| ⅔$H_3PO_4$ | 15.691 ± 1.571 |

| HA | Skin penetration rate of alpha-lipoic acid ($\mu g/cm^2/h$) |
| --- | --- |
| HCl | 35.456 ± 2.476 |
| HF | 34.673 ± 3.156 |
| HBr | 35.211 ± 3.285 |
| HI | 34.467 ± 2.583 |
| Citric acid | 35.371 ± 3.587 |
| Acetic acid | 35.006 ± 2.892 |
| Benzoic acid | 34.665 ± 3.019 |
| Lactic acid | 35.007 ± 2.879 |
| Butyric acid | 35.178 ± 3.598 |
| ½$H_2SO_4$ | 33.928 ± 2.876 |
| $H_2SO_4$ | 33.780 ± 2.891 |
| ⅓$H_3PO_4$ | 34.321 ± 2.867 |
| ⅔$H_3PO_4$ | 34.691 ± 3.511 |

Tyrosine isopropyl ester•HA

| HA | Skin penetration rate of melatonin ($\mu g/cm^2/h$) |
| --- | --- |
| HCl | 16.313 ± 1.753 |
| HF | 15.765 ± 1.946 |
| HBr | 16.578 ± 2.117 |
| HI | 15.863 ± 1.970 |
| Citric acid | 16.246 ± 2.319 |
| Acetic acid | 15.983 ± 3.471 |
| Benzoic acid | 17.002 ± 3.257 |
| Lactic acid | 16.029 ± 2.467 |
| Butyric acid | 16.125 ± 1.972 |
| ½$H_2SO_4$ | 15.978 ± 2.136 |
| $H_2SO_4$ | 16.632 ± 1.357 |
| ⅓$H_3PO_4$ | 15.848 ± 1.782 |
| ⅔$H_3PO_4$ | 16.156 ± 3.124 |

| HA | Skin penetration rate of lipoic acid ($\mu g/cm^2/h$) |
| --- | --- |
| HCl | 33.613 ± 2.819 |
| HF | 33.613 ± 3.219 |
| HBr | 34.013 ± 3.219 |
| HI | 33.572 ± 3.129 |
| Citric acid | 34.013 ± 2.569 |
| Acetic acid | 33.513 ± 2.319 |
| Benzoic acid | 32.913 ± 4.319 |
| Lactic acid | 32.987 ± 4.212 |
| Butyric acid | 33.452 ± 3.756 |
| ½$H_2SO_4$ | 34.012 ± 2.685 |
| $H_2SO_4$ | 33.567 ± 3.125 |
| ⅓$H_3PO_4$ | 33.25 ± 2.762 |
| ⅔$H_3PO_4$ | 34.124 ± 2.912 |

| 1% melatonin (a suspension) without helper esters | Skin penetration rate of melatonin ($\mu g/cm^2/h$) |
| --- | --- |
| | 1.153 ± 0.111 |

| 0.5% alpha-lipoic acid without helper esters | Skin penetration rate of alpha-lipoic acid ($\mu g/cm^2/h$) |
| --- | --- |
| | 0.071 ± 0.063 |

The ability for a concentrated AI-helper composition to stay entirely dissolved, even at cold temperatures (e.g. 10° C. and 20° C.), allows the AI-helper composition to be used in a wide variety of everyday situations.

Example 2. Transdermal Delivery of Melatonin Using Examples of Melatonin-Helper Compositions Disclosed Herein Control compositions (2.0 ml of 0.15% melatonin suspension in water) were applied to a skin on the neck of a subject (20 cm×20 cm). Various melatonin-helper compositions having 7% helper esters and various melatonin concentrations (depending on the composition volume applied to maintain the total mole of melatonin applied being the same as that of the control compositions) were applied to a skin on the back of a subject (20 cm×20 cm). Plasma level of melatonin was tested at 1 hour, 2 hours, 4 hours, and 8 hours respectively after the administration. Results are shown in FIGS. 1A-1H, and Table 19.

I) Transdermal Delivery of Melatonin Using Melatonin-Helper Compositions Comprising Tryptophan Esters.HCl (0.3 mL, +1% Melatonin in Water, FIG. 1A, Table 19).

Compared to control composition (A), melatonin-helper compositions (B: tryptophan isopropyl ester.HCl; C: tryptophan ethyl ester.HCl; and D: tryptophan butyl ester.HCl) provided more efficient and effective transdermal delivery of melatonin.

Figure 1B:
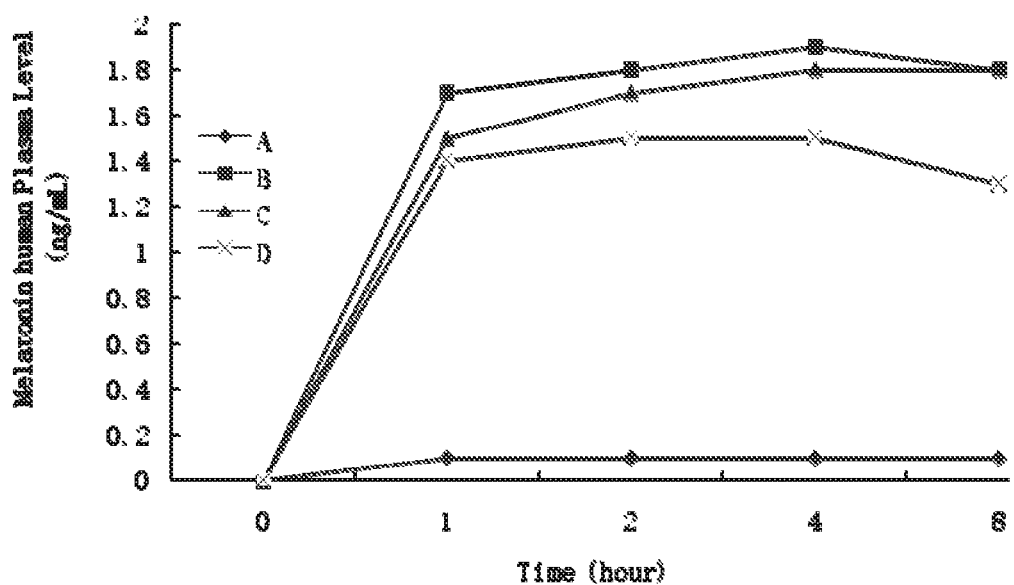
FIG. 1B: Effects of AI-helper compositions comprising leucine esters.HCl at various concentrations as disclosed herein on the human skin penetration rate of the AI, wherein the AI is melatonin.

II) Transdermal Delivery of Melatonin Using Melatonin-Helper Compositions Comprising Leucine Esters.HCl (0.60 mL, +0.5% Melatonin in Water, FIG. 1B, Table 19).

Compared to control composition (A), melatonin-helper compositions (B: leucine isopropyl ester.HCl; C: leucine methyl ester.HCl; and D: leucine hexyl ester.HCl) provided more efficient and effective transdermal delivery of melatonin.

Figure 1C:
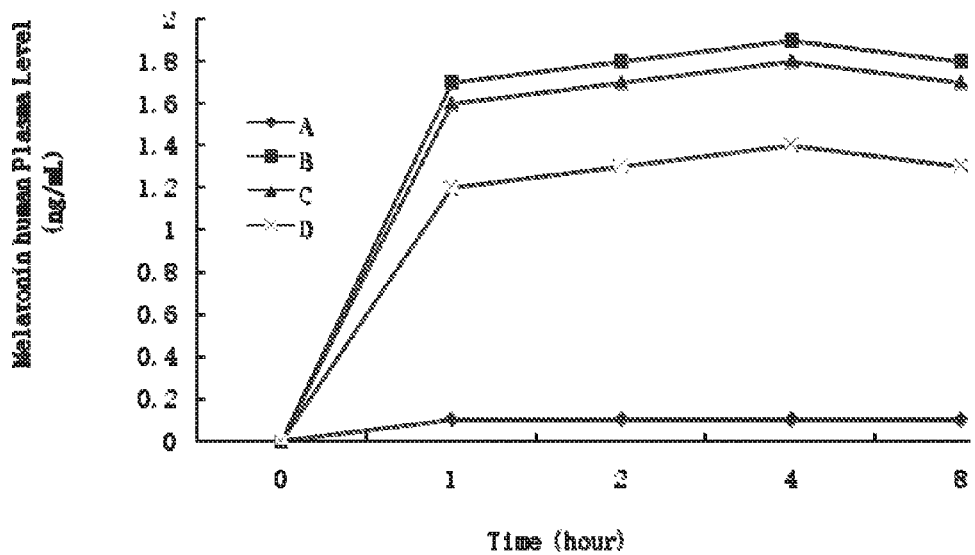
FIG. 1C: Effects of AI-helper compositions comprising isoleucine esters.HCl at various concentrations as disclosed herein on the human skin penetration rate of the AI, wherein the AI is melatonin.

III) Transdermal Delivery of Melatonin Using Melatonin-Helper Compositions Comprising Isoleucine Esters.HCl (0.60 mL, +0.5% Melatonin in Water, FIG. 1C, Table 19).

Compared to control composition (A), melatonin-helper compositions (B: isoleucine isopropyl ester.HCl; C: isoleucine methyl ester.HCl; and D: isoleucine hexyl ester.HCl) provided more efficient and effective transdermal delivery of melatonin.

Figure 1D:
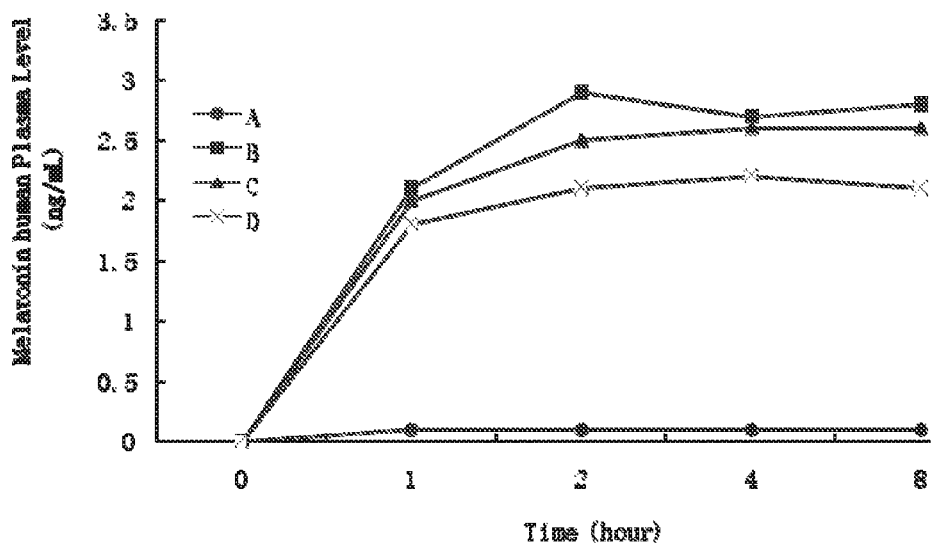
FIG. 1D: Effects of AI-helper compositions comprising tyrosine esters.HCl at various concentrations as disclosed herein on the human skin penetration rate of the AI, wherein the AI is melatonin.

IV) Transdermal Delivery of Melatonin Using Melatonin-Helper Compositions Comprising Tyrosine Esters.HCl (0.3 mL, +1% Melatonin in Water, FIG. 1D, Table 19).

Compared to control composition (A), melatonin-helper compositions (B: tyrosine isopropyl ester.HCl; C: tyrosine propyl ester.HCl; and D: tyrosine pentyl ester.HCl) provided more efficient and effective transdermal delivery of melatonin.

Figure 1E:
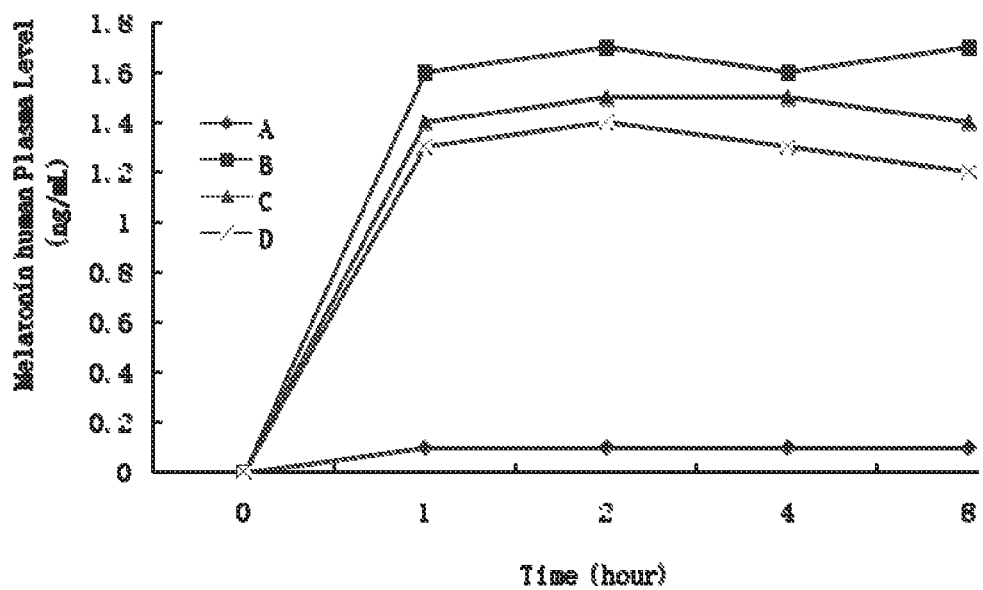
FIG. 1E: Effects of AI-helper compositions comprising phenylalanine esters.HCl at various concentrations as disclosed herein on the human skin penetration rate of the AI, wherein the AI is melatonin.

V) Transdermal Delivery of Melatonin Using Melatonin-Helper Compositions Comprising Phenylalanine Esters.HCl (0.60 mL, +0.5% Melatonin in Water, FIG. 1E, Table 19).

Compared to control composition (A), melatonin-helper compositions (B: phenylalanine isopropyl ester.HCl; C: phenylalanine methyl ester.HCl; and D: phenylalanine octyl ester.HCl) provided more efficient and effective transdermal delivery of melatonin.

Figure 1F:
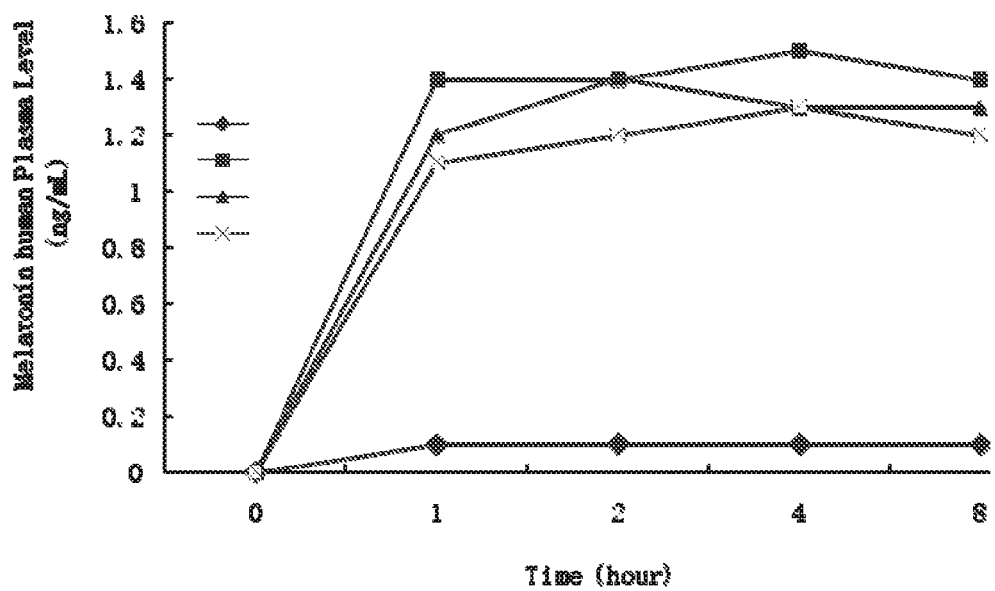
FIG. 1F: Effects of AI-helper compositions comprising proline esters.HCl at various concentrations as disclosed herein on the human skin penetration rate of the AI, wherein the AI is melatonin.

VI) Transdermal Delivery of Melatonin Using Melatonin-Helper Compositions Comprising Proline Esters.HCl (0.60 mL, +0.5% Melatonin in Water, FIG. 1F, Table 19).

Compared to control composition (A), melatonin-helper compositions (B: proline isopropyl ester.HCl; C: proline methyl ester.HCl; and D: proline hexyl ester.HCl) provided more efficient and effective transdermal delivery of melatonin.

Figure 1G:
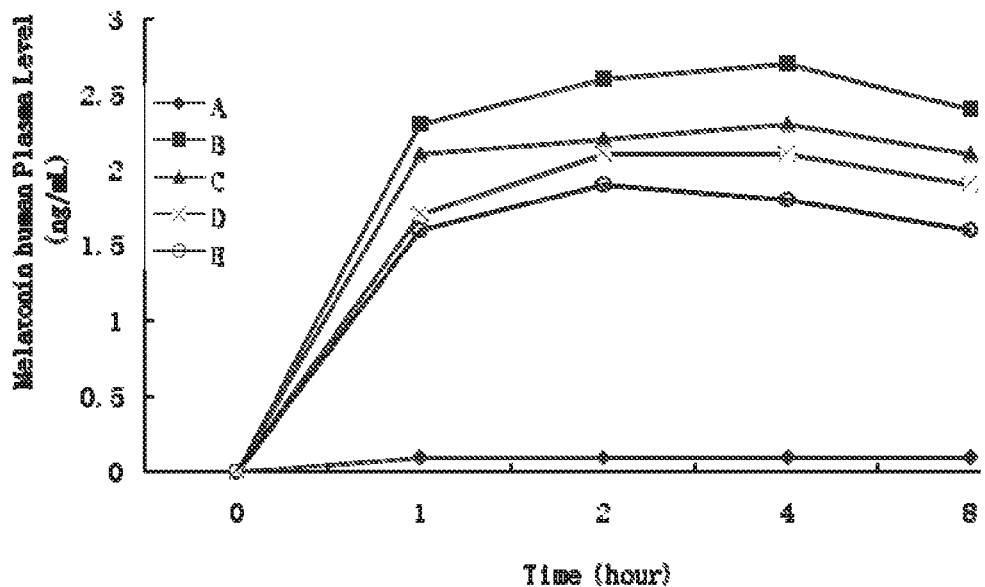
FIG. 1G: Effects of AI-helper compositions comprising (dialkylamino)alkyl 2-acetoxybenzoate hydrochloride at various concentrations as disclosed herein on the human skin penetration rate of the AI, wherein the AI is melatonin.

VII) Transdermal Delivery of Melatonin Using Melatonin-Helper Compositions Comprising (Dialkylamino) Alkyl 2-Acetoxybenzoate Hydrochloride (0.375 mL, +0.8% Melatonin in Water, FIG. 1G, Table 19).

Compared to control composition (A), melatonin-helper compositions (B: 2-(diethylamino)ethyl 2-acetoxybenzoate hydrochloride; C: 3-(diethylamino)propyl 2-acetoxybenzoate hydrochloride; D: 6-(dimethylamino)hexyl 2-acetoxybenzoate hydrochloride; and E: 2-(dibutylamino)ethyl 2-acetoxybenzoate hydrochloride) provided more efficient and effective transdermal delivery of melatonin.

Figure 1H:
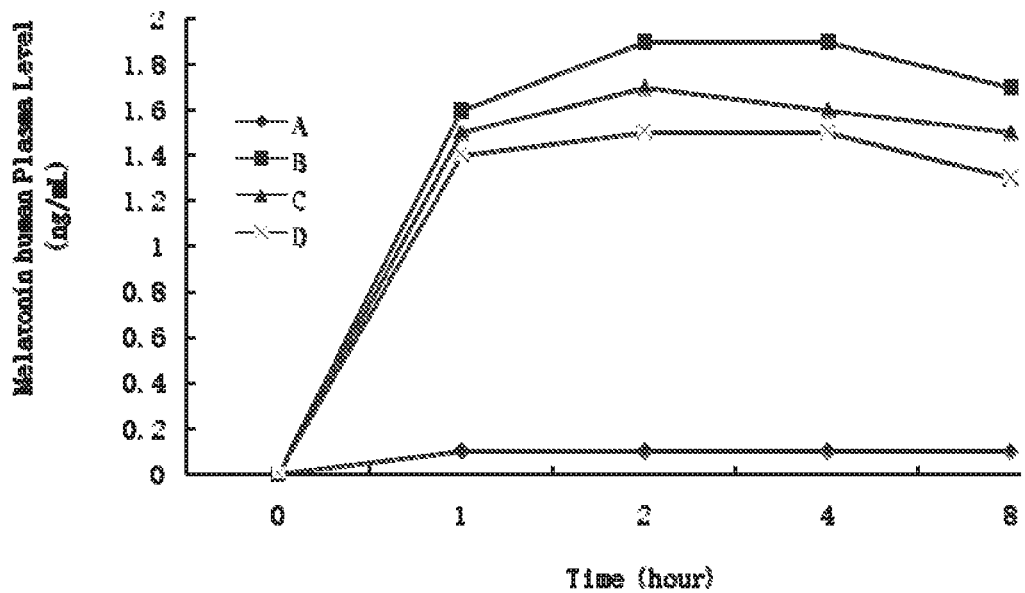
FIG. 1H: Effects of AI-helper compositions comprising (dialkylamino)alkyl 2-(4-isobutylphenyl)propionate hydrochloride at various concentrations as disclosed herein on the human skin penetration rate of the AI, wherein the AI is melatonin.

VIII) Transdermal Delivery of Melatonin Using Melatonin-Helper Compositions Comprising (Dialkylamino) Alkyl 2-(4-Isobutylphenyl)Propionate Hydrochloride (0.60 mL, +0.5% Melatonin in Water, FIG. 1H, Table 19).

Compared to control composition (A), melatonin-helper compositions (B: 5-(diethylamino)pentyl 2-(4-isobutylphenyl)propionate hydrochloride; C: 2-(dimethylamino)ethyl 2-(4-isobutylphenyl)propionate hydrochloride; and D: 4-(diethylamino)butyl 2-(4-isobutylphenyl)propionate hydrochloride) provided more efficient and effective transdermal delivery of melatonin.

TABLE 19

Transdermal delivery of melatonin (12.9 moles of melatonin applied to the skin of the subject) using melatonin-helper compositions (FIGS. 1A-1H)

| Helper esters before Esterification | Helper esters | Total volume applied (mL) | Concentration of helper esters (mM) | Time after transdermal administration (hr) | Plasma level of melatonin (ng/mL) |
| --- | --- | --- | --- | --- | --- |
| TRYPTOPHAN | None | 2.0 | 0 | 0 | 0.0 |
| | | | | 1 | 0.1 |
| | | | | 2 | 0.1 |
| | | | | 4 | 0.1 |
| | | | | 8 | 0.1 |
| | Tryptophan isopropyl ester hydrochloride | 0.3 | 247.52 | 0 | 0.0 |
| | | | | 1 | 2.5 |
| | | | | 2 | 2.8 |
| | | | | 4 | 2.7 |
| | | | | 8 | 2.5 |
| | Tryptophan ethyl ester hydrochloride | 0.3 | 260.47 | 0 | 0 |
| | | | | 1 | 2.0 |
| | | | | 2 | 2.2 |
| | | | | 4 | 1.9 |
| | | | | 8 | 1.8 |

TABLE 19-continued

Transdermal delivery of melatonin (12.9 moles of melatonin applied to the skin of the subject) using melatonin-helper compositions (FIGS. 1A-1H)

| Helper esters before Esterification | Helper esters | Total volume applied (mL) | Concentration of helper esters (mM) | Time after transdermal administration (hr) | Plasma level of melatonin (ng/mL) |
|---|---|---|---|---|---|
| | Tryptophan butyl ester hydrochloride | 0.3 | 235.90 | 0 | 0 |
| | | | | 1 | 1.8 |
| | | | | 2 | 1.9 |
| | | | | 4 | 1.7 |
| | | | | 8 | 1.7 |
| LEUCINE | None | 2 | 0 | 0 | 0 |
| | | | | 1 | 0.1 |
| | | | | 2 | 0.1 |
| | | | | 4 | 0.1 |
| | | | | 8 | 0.1 |
| | Leucine isopropyl ester hydrochloride | 0.60 | 333.76 | 0 | 0 |
| | | | | 1 | 1.7 |
| | | | | 2 | 1.8 |
| | | | | 4 | 1.9 |
| | | | | 8 | 1.8 |
| | Leucine methyl ester hydrochloride | 0.60 | 385.28 | 0 | 0 |
| | | | | 1 | 1.5 |
| | | | | 2 | 1.7 |
| | | | | 4 | 1.8 |
| | | | | 8 | 1.8 |
| | Leucine hexyl ester hydrochloride | 0.60 | 278.04 | 0 | 0 |
| | | | | 1 | 1.4 |
| | | | | 2 | 1.5 |
| | | | | 4 | 1.5 |
| | | | | 8 | 1.3 |
| ISOLEUCINE | None | 2.00 | 0 | 0 | 0 |
| | | | | 1 | 0.1 |
| | | | | 2 | 0.1 |
| | | | | 4 | 0.1 |
| | | | | 8 | 0.1 |
| | Isoleucine isopropyl ester | 0.60 | 333.76 | 0 | 0 |
| | | | | 1 | 1.7 |
| | | | | 2 | 1.8 |
| | | | | 4 | 1.9 |
| | | | | 8 | 1.8 |
| | Isoleucine methyl ester | 0.60 | 385.28 | 0 | 0 |
| | | | | 1 | 1.6 |
| | | | | 2 | 1.7 |
| | | | | 4 | 1.8 |
| | | | | 8 | 1.7 |
| | Isoleucine hexyl ester | 0.60 | 278.04 | 0 | 0 |
| | | | | 1 | 1.2 |
| | | | | 2 | 1.3 |
| | | | | 4 | 1.4 |
| | | | | 8 | 1.3 |
| TYROSINE | None | 2.00 | 0 | 0 | 0 |
| | | | | 1 | 0.1 |
| | | | | 2 | 0.1 |
| | | | | 4 | 0.1 |
| | | | | 8 | 0.1 |
| | Tyrosine isopropyl ester | 0.30 | 269.50 | 0 | 0 |
| | | | | 1 | 2.1 |
| | | | | 2 | 2.9 |
| | | | | 4 | 2.7 |
| | | | | 8 | 2.8 |
| | Tyrosine propyl ester | 0.30 | 269.5 | 0 | 0 |
| | | | | 1 | 2 |
| | | | | 2 | 2.5 |
| | | | | 4 | 2.6 |
| | | | | 8 | 2.6 |
| | Tyrosine pentyl ester | 0.30 | 243.25 | 0 | 0 |
| | | | | 1 | 1.8 |
| | | | | 2 | 2.1 |
| | | | | 4 | 2.2 |
| | | | | 8 | 2.1 |

TABLE 19-continued

Transdermal delivery of melatonin (12.9 moles of melatonin applied to
the skin of the subject) using melatonin-helper compositions (FIGS. 1A-1H)

| Helper esters before Esterification | Helper esters | Total volume applied (mL) | Concentration of helper esters (mM) | Time after transdermal administration (hr) | Plasma level of melatonin (ng/mL) |
|---|---|---|---|---|---|
| PHENYLALANINE | None | 2.00 | 0 | 0 | 0 |
| | | | | 1 | 0.1 |
| | | | | 2 | 0.1 |
| | | | | 4 | 0.1 |
| | | | | 8 | 0.1 |
| | Phenylalanine isopropyl ester hydrochloride | 0.60 | 287.21 | 0 | 0 |
| | | | | 1 | 1.6 |
| | | | | 2 | 1.7 |
| | | | | 4 | 1.6 |
| | | | | 8 | 1.7 |
| | Phenylalanine methyl ester hydrochloride | 0.60 | 324.52 | 0 | 0 |
| | | | | 1 | 1.4 |
| | | | | 2 | 1.5 |
| | | | | 4 | 1.5 |
| | | | | 8 | 1.4 |
| | Phenylalanine octyl ester hydrochloride | 0.60 | 223.02 | 0 | 0 |
| | | | | 1 | 1.3 |
| | | | | 2 | 1.4 |
| | | | | 4 | 1.3 |
| | | | | 8 | 1.2 |
| PROLINE | None | 2.00 | 0 | 0 | 0 |
| | | | | 1 | 0.1 |
| | | | | 2 | 0.1 |
| | | | | 4 | 0.1 |
| | | | | 8 | 0.1 |
| | Proline isopropyl ester hydrochloride | 0.60 | 361.41 | 0 | 0 |
| | | | | 1 | 1.4 |
| | | | | 2 | 1.4 |
| | | | | 4 | 1.5 |
| | | | | 8 | 1.4 |
| | Proline methyl ester hydrochloride | 0.60 | 422.66 | 0 | 0 |
| | | | | 1 | 1.2 |
| | | | | 2 | 1.4 |
| | | | | 4 | 1.3 |
| | | | | 8 | 1.3 |
| | Proline hexyl ester hydrochloride | 0.60 | 296.94 | 0 | 0 |
| | | | | 1 | 1.1 |
| | | | | 2 | 1.2 |
| | | | | 4 | 1.3 |
| | | | | 8 | 1.2 |
| 2-(DIALKYLAMINO) ALKYL 2-ACETOXYBENZOATE | None | 2.00 | 0 | 0 | 0 |
| | | | | 1 | 0.1 |
| | | | | 2 | 0.1 |
| | | | | 4 | 0.1 |
| | | | | 8 | 0.1 |
| | 2-(Diethylamino)ethyl 2-acetoxybenzoate hydrochloride | 0.375 | 221.69 | 0 | 0 |
| | | | | 1 | 2.3 |
| | | | | 2 | 2.6 |
| | | | | 4 | 2.7 |
| | | | | 8 | 2.4 |
| | 3-(Diethylamino)propyl 2-acetoxybenzoate hydrochloride | 0.375 | 212.24 | 0 | 0 |
| | | | | 1 | 2.1 |
| | | | | 2 | 2.2 |
| | | | | 4 | 2.3 |
| | | | | 8 | 2.1 |
| | 6-(Dimethylamino) hexyl 2-acetoxybenzoate hydrochloride | 0.375 | 203.56 | 0 | 0 |
| | | | | 1 | 1.7 |
| | | | | 2 | 2.1 |
| | | | | 4 | 2.1 |
| | | | | 8 | 1.9 |
| | 2-(Dibutylamino)ethyl 2-acetoxybenzoate hydrochloride | 0.375 | 188.23 | 0 | 0 |
| | | | | 1 | 1.6 |
| | | | | 2 | 1.9 |
| | | | | 4 | 1.8 |
| | | | | 8 | 1.6 |

TABLE 19-continued

Transdermal delivery of melatonin (12.9 moles of melatonin applied to the skin of the subject) using melatonin-helper compositions (FIGS. 1A-1H)

| Helper esters before Esterification | Helper esters | Total volume applied (mL) | Concentration of helper esters (mM) | Time after transdermal administration (hr) | Plasma level of melatonin (ng/mL) |
|---|---|---|---|---|---|
| 2-(DIALKYLAMINO)ALKYL 2-(4-ISOBUTYLPHENYL)PROPIONATE | None | 2.00 | 0 | 0 | 0 |
| | | | | 1 | 0.1 |
| | | | | 2 | 0.1 |
| | | | | 4 | 0.1 |
| | | | | 8 | 0.1 |
| | 5-(Diethylamino)pentyl 2-(4-isobutylphenyl)propionate hydrochloride | 0.60 | 182.28 | 0 | 0 |
| | | | | 1 | 1.6 |
| | | | | 2 | 1.9 |
| | | | | 4 | 1.9 |
| | | | | 8 | 1.7 |
| | 2-(Dimethylamino)ethyl 2-(4-isobutylphenyl)propionate hydrochloride | 0.60 | 222.60 | 0 | 0 |
| | | | | 1 | 1.5 |
| | | | | 2 | 1.7 |
| | | | | 4 | 1.6 |
| | | | | 8 | 1.5 |
| | 4-(Diethylamino)butyl 2-(4-isobutylphenyl)propionate hydrochloride | 0.60 | 189.21 | 0 | 0 |
| | | | | 1 | 1.4 |
| | | | | 2 | 1.5 |
| | | | | 4 | 1.5 |
| | | | | 8 | 1.3 |

Figure 2A:
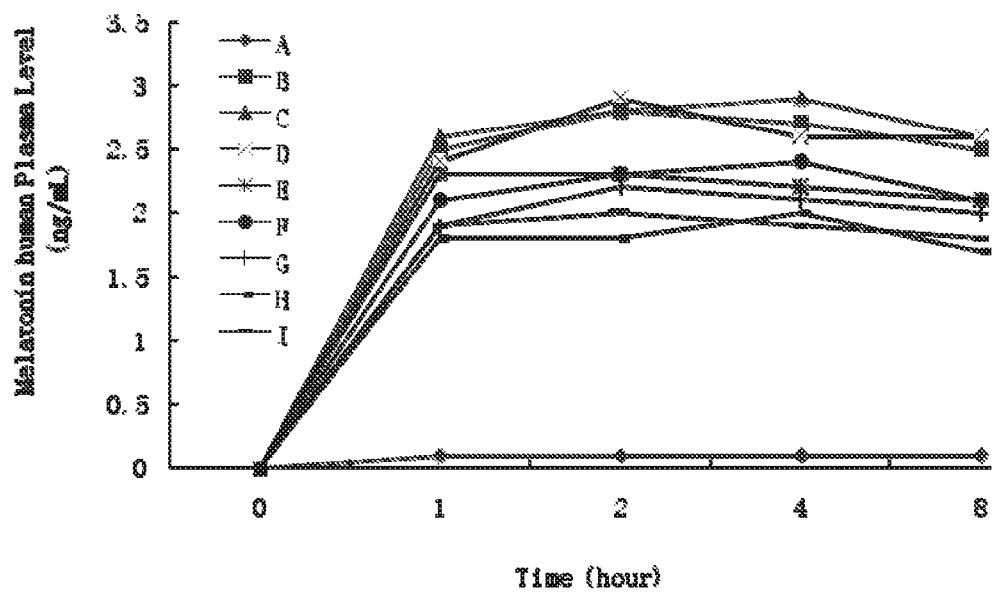
FIG. 2A: Effects of melatonin-helper compositions comprising different salts of tryptophan isopropyl esters on the human skin penetration rate of melatonin. (A). Control; (B). hydrochloride salt; (C). hydrofluoride salt; (D). hydrobromide salt; (E). hydroiodide salt; (F). citrate salt; (G). acetate salt; (H). benzoate salt; and (I). lactate salt.
Figure 2B:
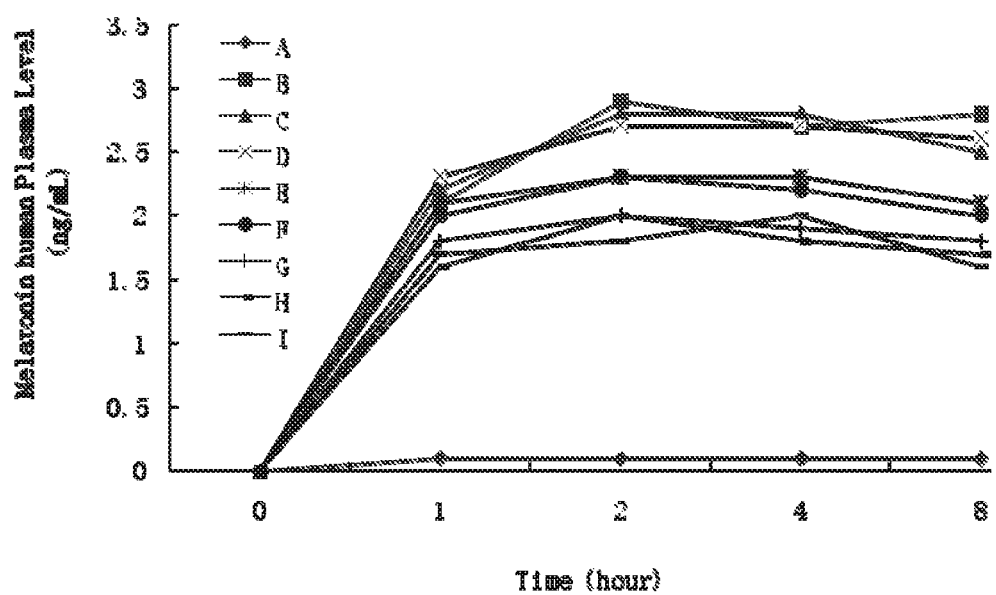
FIG. 2B: Effects of melatonin-helper compositions comprising different salts of tyrosine isopropyl esters on the human skin penetration rate of melatonin. (A). Control; (B). hydrochloride salt; (C). hydrofluoride salt; (D). hydrobromide salt; (E). hydroiodide salt; (F). citrate salt; (G). acetate salt; (H). benzoate salt; and (I). lactate salt.

Example 3. Transdermal Delivery of Melatonin Using Melatonin-Helper Compositions Comprising Various Salts of Tryptophan Isopropyl Ester (FIG. 2A, Table 20) or Tyrosine Isopropyl Ester (FIG. 2B, Table 21) as the Helper Esters In certain embodiments, melatonin-helper compositions comprising various salts of the helper esters disclosed herein formed with various acids showed similar improvements in transdermal delivery of melatonin (FIGS. 2A and 2B, Tables 20 and 21).

Control composition (2.0 ml of 0.15% melatonin suspension in water) was applied to a skin on the neck of a subject (20 cm×20 cm). Various melatonin-helper compositions (0.30 mL, 7% helper esters and 1% melatonin in water) were applied to a skin on the back of a subject (20 cm×20 cm). Plasma level of melatonin was tested at 1 hour, 2 hours, 4 hours, and 8 hours respectively after the administration. Results are shown in FIG. 2A and Table 20 when the helper ester is tryptophan isopropyl ester, and in FIG. 2A and Table 20 when the helper ester is tyrosine isopropyl ester.

Compared to control composition (A), melatonin-helper compositions (B: hydrochloride salt; C: hydrofluoride salt; D: HBr salt; E: HI salt; F: citratre salt; G: acetate salt; H: benzoate salt; and I: lactate salt) provided more efficient and effective transdermal delivery of melatonin.

TABLE 20

Transdermal delivery of melatonin (12.9 moles of melatonin applied to the skin of the subject) using melatonin-helper compositions comprising various salts of tryptophan isopropyl ester (FIG. 2A)

| A- | Total volume applied (mL) | Concentration of helper esters (mM) | Time after transdermal administration (hr) | Plasma level of melatonin (ng/mL) |
|---|---|---|---|---|
| N/A | 2.0 | 0 | 0 | 0 |
| | | | 1 | 0.1 |
| | | | 2 | 0.1 |
| | | | 4 | 0.1 |
| | | | 8 | 0.1 |
| Cl− | 0.30 | 247.52 | 0 | 0 |
| | | | 1 | 2.5 |
| | | | 2 | 2.8 |
| | | | 4 | 2.7 |
| | | | 8 | 2.5 |
| F− | 0.30 | 262.85 | 0 | 0 |
| | | | 1 | 2.6 |
| | | | 2 | 2.8 |
| | | | 4 | 2.9 |
| | | | 8 | 2.6 |
| Br− | 0.30 | 220.92 | 0 | 0 |
| | | | 1 | 2.4 |
| | | | 2 | 2.9 |
| | | | 4 | 2.6 |
| | | | 8 | 2.6 |
| I− | 0.30 | 187.04 | 0 | 0 |
| | | | 1 | 2.3 |
| | | | 2 | 2.3 |
| | | | 4 | 2.2 |
| | | | 8 | 2.1 |
| Citrate ion | 0.30 | 159.67 | 0 | 0 |
| | | | 1 | 2.1 |
| | | | 2 | 2.3 |
| | | | 4 | 2.4 |
| | | | 8 | 2.1 |
| AcO− | 0.30 | 228.48 | 0 | 0 |
| | | | 1 | 1.9 |
| | | | 2 | 2.2 |
| | | | 4 | 2.1 |
| | | | 8 | 2.0 |

TABLE 20-continued

Transdermal delivery of melatonin (12.9 moles of melatonin applied to the skin of the subject) using melatonin-helper compositions comprising various salts of tryptophan isopropyl ester (FIG. 2A)

| A− | Total volume applied (mL) | Concentration of helper esters (mM) | Time after transdermal administration (hr) | Plasma level of melatonin (ng/mL) |
|---|---|---|---|---|
| Benzoate ion | 0.30 | 189.98 | 0 | 0 |
| | | | 1 | 1.8 |
| | | | 2 | 1.8 |
| | | | 4 | 2.0 |
| | | | 8 | 1.7 |
| Lactate ion | 0.30 | 208.11 | 0 | 0 |
| | | | 1 | 1.9 |
| | | | 2 | 2.0 |
| | | | 4 | 1.9 |
| | | | 8 | 1.8 |

TABLE 21

Transdermal delivery of melatonin (12.9 moles of melatonin applied to the skin of the subject) using melatonin-helper compositions comprising various salts of tyrosine isopropyl ester (FIG. 2B)

| A− | Total volume applied (mL) | Concentration of helper esters (mM) | Time after transdermal administration (hr) | Plasma level of melatonin (ng/mL) |
|---|---|---|---|---|
| N/A | 2.0 | 0 | 0 | 0 |
| | | | 1 | 0.1 |
| | | | 2 | 0.1 |
| | | | 4 | 0.1 |
| | | | 8 | 0.1 |
| Cl− | 0.30 | 269.51 | 0 | 0 |
| | | | 1 | 2.1 |
| | | | 2 | 2.9 |
| | | | 4 | 2.7 |
| | | | 8 | 2.8 |
| F− | 0.30 | 287.91 | 0 | 0 |
| | | | 1 | 2.2 |
| | | | 2 | 2.8 |
| | | | 4 | 2.8 |
| | | | 8 | 2.5 |
| Br− | 0.30 | 230.16 | 0 | 0 |
| | | | 1 | 2.3 |
| | | | 2 | 2.7 |
| | | | 4 | 2.7 |
| | | | 8 | 2.6 |
| I− | 0.30 | 199.43 | 0 | 0 |
| | | | 1 | 2.1 |
| | | | 2 | 2.3 |
| | | | 4 | 2.3 |
| | | | 8 | 2.1 |
| Citrate ion | 0.30 | 168.49 | 0 | 0 |
| | | | 1 | 2.0 |
| | | | 2 | 2.3 |
| | | | 4 | 2.2 |
| | | | 8 | 2.0 |
| AcO− | 0.30 | 245.0 | 0 | 0 |
| | | | 1 | 1.8 |
| | | | 2 | 2.0 |
| | | | 4 | 1.9 |
| | | | 8 | 21.8 |
| Benzoate ion | 0.30 | 202.65 | 0 | 0 |
| | | | 1 | 1.6 |
| | | | 2 | 2.0 |
| | | | 4 | 1.8 |
| | | | 8 | 1.7 |
| Lactate ion | 0.30 | 221.97 | 0 | 0 |
| | | | 1 | 1.7 |
| | | | 2 | 1.8 |
| | | | 4 | 2.0 |
| | | | 8 | 1.6 |

Thus, melatonin-helper compositions comprising salts of the helper esters disclosed herein formed with any acid that is non-toxic for humans and animals (e.g. pharmaceutically acceptable acids, as described supra) should also improve the transdermal delivery of melatonin.

Example 4. Preparations of Helper Esters

Other helper esters (e.g. esters of amino acids or other acids (e.g. (dialkylamino)ethyl 2-(4-isobutylphenyl)propionate and 2-(dialkylamino)alkyl 2-acetoxybenzoate), and pharmaceutically acceptable salts thereof (e.g. hydrochlorides thereof)) may be prepared by similar methods as described below.

I) Preparation of Tyrosine Isopropyl Ester.HCl

Tyrosine (1 kg) was suspended in isopropanol (5 L) in a 10 L flask. HCl gas (350 g) was bubbled into the reaction mixture. The mixture was stirred for 2 days at 50° C. The solvent was evaporated off at below 40° C., and fresh isopropanol (4 L) was added into the residue. The mixture was stirred for 1 day at 50° C. The solvent was evaporated off at below 40° C., and isopropyl acetate (3 L) was added into the residue. The solid was collected by filtration and washed with isopropyl acetate (3×1 L). The solid was dried in a vacuum oven at 50° C.

II) Preparation of D-Tyrosine Isopropyl Ester.HCl

D-Tyrosine (1 kg) was suspended in isopropanol (5 L) in a 10 L flask. HCl gas (350 g) was bubbled into the reaction mixture. The mixture was stirred for 2 days at 50° C. The solvent was evaporated off at below 40° C., and fresh isopropanol (4 L) was added into the residue. The mixture was stirred for 1 day at 50° C. The solvent was evaporated off at below 40° C., and isopropyl acetate (3 L) was added into the residue. The solid was collected by filtration and washed with isopropyl acetate (3×1 L). The solid was dried in a vacuum oven at 50° C.

III) Preparation of 2-(diethylamino)ethyl 2-(4-isobutylphenyl)propionate hydrochloride 2-(4-isobutylphenyl)propionoic acid (4120 g) was dissolved in ethyl acetate (R0061, 4 L) and thionyl chloride (1750 ml). The mixture was refluxed for 3 h. The mixture was evaporated to dryness completely. Isopropyl acetate (3 L) was added into the residue and the mixture was evaporated to dryness. Isopropyl acetate (3 L) was added into the residue and evaporated off. Isopropyl acetate (20 L) was added into the reaction mixture. The mixture was cooled to 5° C. in an ice-water bath. N,N-diethylaminoethanol (2340 g) was added into the reaction mixture drop by drop. $K_2CO_3$ (2800 g) was added into the reaction mixture slowly. The mixture was stirred overnight at room temperature. Water (10 L) was added into the mixture. The ethyl acetate mixture was collected and washed with 5% $NaHCO_3$ (1×7 L) and water (3×6 L) and dried over $Na_2SO_4$. Sodium sulfate was removed by filtration and washed with isopropyl acetate (3×1 L). HCl gas (700 g) was added into the mixture and stirred. The solid was collected and washed with isopropyl acetate (3×2 L). The product was dried in a vacuum oven at 45° C.

Example 5. The Preparation of Composition 1

Tryptophan ethyl ester.HCl (70 g) was dissolved in water (1 L). Melatonin (10 g) was added into the mixture and the mixture was stirred until a clear solution was formed. The mixture was filled into either spray bottles or roll-on bottles.

Example 6. The Preparation of Composition 2

D-Tryptophan ethyl ester.HCl (70 g) was dissolved in water (1 L). Melatonin (10 g) was added into the mixture and the mixture was stirred until a clear solution was formed. The mixture was filled into either spray bottles or roll-on bottles.

Example 7. The Preparation of Composition 3

Tyrosine isopropyl ester.HBr (70 g) was dissolved in water (1 L). Melatonin (10 g) were added into the mixture and the mixture was stirred until a clear solution was formed. The mixture was filled into either spray bottles or roll-on bottles.

Example 8. The Preparation of Composition 4

Tyrosine isopropyl ester.lactic acid (70 g) was dissolved in water (1 L). Melatonin (10 g) and ethanol (100 ml) were added into the mixture and the mixture was stirred until a clear solution was formed. The mixture was filled into either spray bottles or roll-on bottles.

Example 9. The Preparation of Composition 5

Tyrosine isopropyl ester.HCl (70 g) was dissolved in water (1 L). Melatonin (6 g) were added into the mixture and the mixture was stirred until a clear solution was formed. The mixture was filled into either spray bottles or roll-on bottles.

Example 10. The Preparation of Composition 6

Leucine isopropyl ester.HCl (100 g) was dissolved in water (1 L). Melatonin (5 g) were added into the mixture and the mixture was stirred until a clear solution was formed. The mixture was filled into either spray bottles or roll-on bottles.

Example 11. The Preparation of Composition 7

Isoleucine isopropyl ester.HCl (70 g) was dissolved in water (1 L). Melatonin (5 g) were added into the mixture and the mixture was stirred until a clear solution was formed. The mixture was filled into either spray bottles or roll-on bottles.

Example 12. The Preparation of Composition 8

Tyrosine isopropyl ester.HCl (70 g) was dissolved in water (1 L). Melatonin (7 g) were added into the mixture and the mixture was stirred until a clear solution was formed. The mixture was filled into either spray bottles or roll-on bottles.

Example 13. The Preparation of Composition 9

Tyrosine isopropyl ester.HCl (70 g) was dissolved in water (1 L). Melatonin (6 g) were added into the mixture and the mixture was stirred for a few minutes. The mixture was filled into either spray bottles or roll-on bottles.

Example 14. The Preparation of Composition 10

Tyrosine isopropyl ester.HCl (70 g) was dissolved in water (1 L). Melatonin (g)10, and ethanol (100 ml) were added into the mixture and the mixture was stirred until a clear solution was formed. The mixture was filled into either spray bottles or roll-on bottles.

Example 15. The Preparation of Composition 11

Proline ethyl ester.HCl (100 g) was dissolved in water (1 L). Melatonin (5 g) was added into the mixture and the mixture was stirred until a clear solution was formed. The mixture was filled into either spray bottles or roll-on bottles.

Example 16. The Preparation of Composition 12

Tyrosine isopropyl ester.HCl (70 g) and tyrosine (7 g) were dissolved in water (1 L). Melatonin (8 g) and ethanol (100 ml) were added into the mixture and the mixture was stirred until a clear solution was formed. The mixture was filled into either spray bottles or roll-on bottles.

Example 17. The Preparation of Composition 13

Tyrosine isopropyl ester.HCl (70 g) and tyrosine (7 g) were dissolved in water (1 L). Melatonin (8 g) was added into the mixture and the mixture was stirred until a clear solution was formed. The mixture was filled into either spray bottles or roll-on bottles.

Example 18. The Preparation of Composition 14

Tryptophan isopropyl ester.HBr (120 g) and tryptophan (5 g) were dissolved in water (1 L). Melatonin (10 g) and ethanol (100 mL) were added into the mixture and the mixture was stirred until a clear solution was formed. The mixture was filled into either spray bottles or roll-on bottles.

Example 19. The Preparation of Composition 15

Valine ethyl ester.HCl (100 g) was dissolved in water (1 L). Melatonin (5 g) and DMSO (200 ml) were added into the mixture and the mixture was stirred until a clear solution was formed. The mixture was filled into either spray bottles or roll-on bottles.

Example 20. The Preparation of Composition 16

Valine ethyl ester.HCl (100 g) was dissolved in water (1 L). Melatonin (5 g) and DMSO (200 ml) were added into the mixture and the mixture was stirred until a clear solution was formed. The mixture was filled into either spray bottles or roll-on bottles.

Example 21. The Preparation of Composition 17

Phenylalanine butyl ester.HCl (100 g) was dissolved in water (1 L). Melatonin (5 g) and glycerin (100 ml) were added into the mixture and the mixture was stirred until a clear solution was formed. The mixture was filled into either spray bottles or roll-on bottles.

Example 22. The Preparation of Composition 18

Phenylalanine butyl ester.HCl (100 g) was dissolved in water (1 L). Melatonin (5 g) and sodium benzoate (50 g) were added into the mixture and the mixture was stirred until a clear solution was formed. The mixture was filled into either spray bottles or roll-on bottles.

Example 23. The Preparation of Composition 19

2-(diethylamino)propyl 2-acetoxybenzoate hydrochloride (100 g) was dissolved in water (1 L). Melatonin (5 g) and glycerin (100 ml) were added into the mixture and the mixture was stirred until a clear solution is formed. The mixture was filled into either spray bottles or roll-on bottles.

Example 24. The Preparation of Composition 20

2-(diethylamino)propyl 2-acetoxybenzoate hydrochloride (70 g) was dissolved in water (1 L). Melatonin (6 g) was added into the mixture and the mixture was stirred until a clear solution was formed. The mixture was filled either into spray bottles or roll-on bottles.

Example 25. The Preparation of Composition 21

Tryptophan isopropyl ester.HBr (100 g) was dissolved in water (1 L). Melatonin (10 g) was added into the mixture and the mixture was stirred until a clear solution was formed. The mixture was filled into either spray bottles or roll-on bottles.

Example 26. The Preparation of Composition 22

Tryptophan isopropyl ester.lactic acid (80 g) was dissolved in water (1 L). Melatonin (10 g) was added into the mixture and the mixture was stirred until a clear solution was formed. The mixture was filled into either spray bottles or roll-on bottles.

Example 27. The Preparation of Composition 23

Tryptophan isopropyl ester.HCl (70 g) was dissolved in water (1 L). Melatonin (5 g) was added into the mixture and the mixture was stirred until a clear solution was formed. The mixture was filled into either spray bottles or roll-on bottles.

Example 28. The Preparation of Composition 24

Leucine isopropyl ester.HCl (100 g) was dissolved in water (1 L). Melatonin (5 g) and acetone (100 mL) were added into the mixture and the mixture was stirred until a clear solution was formed. The mixture was filled into either spray bottles or roll-on bottles.

Example 29. The Preparation of Composition 25

Isoleucine isopropyl ester.HCl (100 g) was dissolved in water (1 L). Melatonin (7 g) and isopropanol (100 mL) were added into the mixture and the mixture was stirred until a clear solution was formed. The mixture was filled into either spray bottles or roll-on bottles.

Example 30. The Preparation of Composition 26

Tyrosine isopropyl ester.HCl (120 g) was dissolved in water (1 L). Melatonin (10 g) was added into the mixture and the mixture was stirred until a clear solution was formed. The mixture was filled into either spray bottles or roll-on bottles.

Example 31. The Preparation of Composition 27

Tyrosine isopropyl ester.HCl (70 g) was dissolved in water (1 L). Melatonin (6 g) and ethanol (300 mL) added into the mixture and the mixture was stirred until a clear solution was formed. The mixture was filled into either spray bottles or roll-on bottles.

Example 32. The Preparation of Composition 28

Tyrosine isopropyl ester.HCl (70 g) was dissolved in water (1 L). Melatonin (10 g) and ethanol (150 mL) were added into the mixture and the mixture was stirred until a clear solution was formed. The mixture was filled into either spray bottles or roll-on bottles.

Example 33. The Preparation of Composition 29

Proline ethyl ester.HCl (100 g) was dissolved in water (1 L). Melatonin (5 g) and DMSO (100 mL) were added into the mixture and the mixture was stirred until a clear solution was formed. The mixture was filled into either spray bottles or roll-on bottles.

Example 34. The Preparation of Composition 30

Tyrosine isopropyl ester.HCl (70 g) and tyrosine (7 g) were dissolved in water (1 L). Melatonin (7 g) was added into the mixture and the mixture was stirred until a clear solution was formed. The mixture was filled into either spray bottles or roll-on bottles.

Example 35. The Preparation of Composition 31

Tyrosine isopropyl ester.HCl (70 g) and tyrosine (7 g) were dissolved in water (1 L). Melatonin (7 g) and ethanol (150 mL) were added into the mixture and the mixture was stirred until a clear solution was formed. The mixture was filled into either spray bottles or roll-on bottles.

Example 36. The Preparation of Composition 32

Tryptophan isopropyl ester.HBr (120 g) and tryptophan (5 g) were dissolved in water (1 L). Melatonin (10 g) and ethanol (10 mL) were added into the mixture and the mixture was stirred for a few minutes. The mixture was filled into either spray bottles or roll-on bottles.

Example 37. The Preparation of Composition 33

Valine ethyl ester.HCl (100 g) was dissolved in water (1 L). Melatonin (5 g) and ethanol (150 mL) were added into the mixture and the mixture was stirred until a clear solution was formed. The mixture was filled into either spray bottles or roll-on bottles.

Example 38. The Preparation of Composition 34

Valine ethyl ester.HCl (60 g) was dissolved in water (1 L). Melatonin (5 g) was added into the mixture and the mixture was stirred until a clear solution was formed. The mixture was filled into either spray bottles or roll-on bottles.

Example 39. The Preparation of Composition 35

Phenylalanine butyl ester.HCl (70 g) was dissolved in water (1 L). Melatonin (7 g) and glycerin (200 ml) were added into the mixture and the mixture was stirred until a clear solution was formed. The mixture was filled into either spray bottles or roll-on bottles.

Example 40. The Preparation of Composition 36

Phenylalanine butyl ester.HCl (70 g) was dissolved in water (1 L). Melatonin (5 g) and sodium benzoate (50 g)

were added into the mixture and the mixture was stirred until a clear solution was formed. The mixture was filled into either spray bottles or roll-on bottles.

Example 41. The Preparation of Composition 37

2-(diethylamino)propyl 2-acetoxybenzoate hydrochloride (70 g) was dissolved in water (1 L). Melatonin (8 g) and glycerin (200 ml) were added into the mixture and the mixture was stirred until a clear solution was formed. The mixture was filled into either spray bottles or roll-on bottles.

What is claimed is:

1. An active ingredient (AI)-helper composition comprising (i) a mixture of one or more helper esters, and an AI compound, pharmaceutically acceptable solvates of the AI compound, or pharmaceutically acceptable salts of the AI compound; or (ii) mixtures of one or more helper esters and the AI compound, the pharmaceutically acceptable solvates of the AI compound, and/or the pharmaceutically acceptable salts of the AI compounds in any ratios; wherein the AI compound is melatonin, wherein the one or more helper esters are selected from the group consisting of Structure 1

Structure 2

Structure 3

Structure 4

Structure 5

Structure 6

Structure 7

Structure 8

Structure 9

Structure 10

Structure 11

-continued

Structure 12
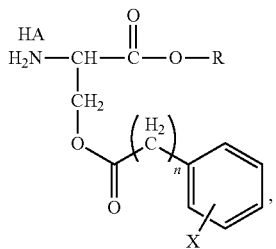

Structure 13
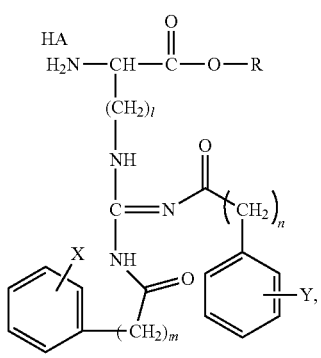

Structure 14
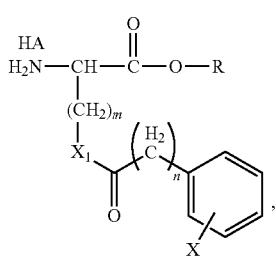

Structure 15
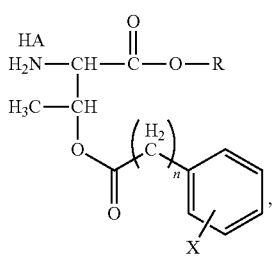

Structure 16
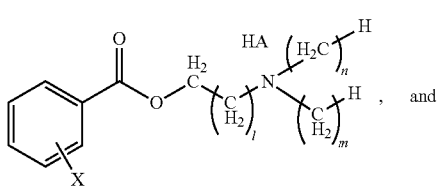

Structure 17
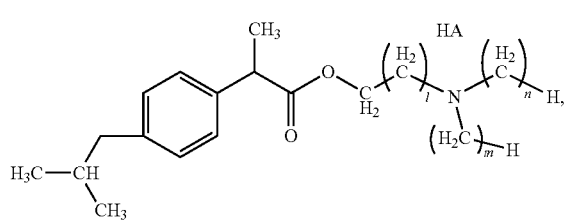

wherein:
each X is independently selected from the group consisting of H, $NH_2$, $NHR_5$, OH, $OCOR_5$, Cl, Br, I, CN, $R_5COS$, $R_5O$, $R_5OCONH$, $CH_2NHR_5$, $R_5SO_2$, $R_5SO$, $NH_2SO_2$, and $NO_2$;
each $X_1$ is independently selected from the group consisting of O, S, $NH_2$, and $NHR_5$;
each $R_5$ and R is independently selected from the group consisting of H, alkyl, cycloalkyl, heterocycloalkyl, aryl, heteroaryl, alkoxyl, alkylthio, alkylamino, perfluoroalkyl, alkyl halide, substituted alkyl, substituted cycloalkyl, substituted heterocycloalkyl, substituted aryl, substituted heteroaryl, substituted alkoxyl, substituted alkylthio, substituted alkylamino, substituted perfluoroalkyl, and substituted alkyl halide, wherein any carbon or hydrogen may be further independently replaced with O, S, P, or NRz;
Rz is selected from the group consisting of H, alkyl, cycloalkyl, heterocycloalkyl, aryl, heteroaryl, alkoxyl, alkylthio, alkylamino, perfluoroalkyl, alkyl halide, substituted alkyl, substituted cycloalkyl, substituted heterocycloalkyl, substituted aryl, substituted heteroaryl, substituted alkoxyl, substituted alkylthio, substituted alkylamino, substituted perfluoroalkyl, and substituted alkyl halide;
each HA is independently selected from the group consisting of pharmaceutically acceptable acids; and
each l, m, and n is independently selected from the group consisting of 0, 1, 2, 3, 4, 5, 6, 7, 8, 9, and 10.

2. The AI-helper composition according to claim 1, wherein the pharmaceutically acceptable acid is selected from the group consisting of HF, HCl, HBr, HI, acetic acid, citric acid, benzoic acid, lactic acid, nitric acid, sulfuric acid, bisulfuric acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid, and pamoic acid.

3. The AI-helper composition according to claim 1, wherein the amount of the AI compound ranges from about 0.01 percent to about 10 percent, from about 0.1 percent to about 5 percent, from about 0.2 percent to about 3 percent, or from about 0.3 percent to about 1 percent of the AI-helper compositions by weight.

4. The AI-helper composition according to claim 1, wherein the amount of the one or more helper esters ranges from about 1 percent to about 50 percent, from about 2 percent to about 25 percent, from about 3 percent to about 10 percent, or from about 4 percent to about 7 percent of the AI-helper composition by weight.

5. The AI-helper composition according to claim 1, further comprising one or more amino acids selected from the group consisting of, L tryptophan, L-leucine, L-isoleucine, L-proline, L-tyrosine, L-phenylalanine, L-arginine, L-alanine, L-asparagine, L-aspartic acid, L-cysteine, L-glutamine, L-histidine, L-lysine, L-methionine, L-serine, L-threonine, L-valine, D-tryptophan, D-leucine, D-isoleucine, D-proline, D-tyrosine, D-phenylalanine, D-arginine, D-alanine, D-asparagine, D-aspartic acid, D-cysteine, D-glutamine, D-histidine, D-lysine, D-methionine, D-serine, D-threonine, D-valine, and glycine.

6. The AI-helper composition according to claim 5, wherein the amount of the one or more amino acids ranges from about 0.001 percent to about 50 percent, from about 0.01 percent to about 20 percent, from about 0.1 percent to about 10 percent, or from about 0.1 percent to about 2 percent of the AI-helper composition by weight.

7. The AI-helper composition according to claim 1, further comprising menthol, wherein the amount of menthol ranges from about 0.01 percent to about 20 percent, from about 0.1 percent to about 10 percent, from about 1 percent to about 5 percent, or from about 1 percent to about 3 percent of the AI-helper composition by weight.

8. The AI-helper composition according to claim 1, further comprising a solvent.

9. The AI-helper composition according to claim 8, wherein the solvent comprises water, and the amount of water ranges from about 1 percent to about 99 percent, from about 50 percent to about 95 percent, from about 75 percent to about 95 percent, or from about 80 percent to about 95 percent of the AI-helper composition by weight.

10. The AI-helper composition according to claim 8, wherein the solvent comprises one or more alcohols, wherein the amount of the one or more alcohols ranges from about 1 percent to about 99 percent, from about 5 percent to about 75 percent, from about 10 percent to about 50 percent, or from about 10 percent to about 25 percent of the AI-helper composition by weight.

11. The AI-helper composition according to claim 10, wherein the one or more alcohols are selected from the group consisting of ethanol, propanol, isopropanol, and butanol.

12. The AI-helper composition according to claim 8, wherein the solvent comprises glycerin, and the amount of glycerin ranges from about 1 percent to about 50 percent, from about 1 percent to about 25 percent, from about 5 percent to about 20 percent, or from about 5 percent to about 10 percent of the AI-helper compositions by weight.

13. The AI-helper composition according to claim 8, wherein the solvent comprises dimethyl sulfoxide (DMSO), and the amount of DMSO ranges from about 1 percent to about 80 percent, from about 5 percent to about 70 percent, from about 10 percent to about 50 percent, or from about 20 percent to about 30 percent of the AI-helper compositions by weight.

14. The AI-helper composition according to claim 1, further comprising one or more adjuvants selected from the group consisting of preservatives, wetting agents, emulsifying agents, dispersing agents, antibacterial agents, and antifungal agents.

15. The AI-helper composition according to claim 14, wherein the antibacterial agents and antifungal agents are selected from the group consisting of paraben, chlorobutanol, and phenol sorbic acid.

16. A method for delivering melatonin to a subject in need thereof comprising administering to the subject the AI-helper composition according to claim 1 by an administration route selected from the group consisting of transdermal, transmucosal, trans-nasal, topical, and any combinations thereof.

17. The method according to claim 16, wherein the AI-helper composition is administered to the subject by spraying or rolling-on to the subject.

* * * * *